United States Patent [19]
Webster, Jr.

[11] Patent Number: 5,614,361
[45] Date of Patent: *Mar. 25, 1997

[54] METHOD FOR IDENTIFYING AND CHARACTERIZING ORGANISMS

[76] Inventor: John A. Webster, Jr., 8343 Carrleigh Parkway, Springfield, Va. 22152

[*] Notice: The portion of the term of this patent subsequent to Jan. 5, 2005, has been disclaimed.

[21] Appl. No.: 208,198

[22] Filed: Mar. 10, 1994

Related U.S. Application Data

[60] Continuation of Ser. No. 731,153, Jul. 15, 1991, abandoned, which is a division of Ser. No. 294,903, Jan. 4, 1989, Pat. No. 5,087,558, which is a continuation of Ser. No. 892,064, Aug. 1, 1986, abandoned, which is a continuation of Ser. No. 477,431, Mar. 21, 1983, abandoned, which is a continuation-in-part of Ser. No. 305,498, Sep. 25, 1981, Pat. No. 4,717,653.

[51] Int. Cl.$^6$ .............................. C12Q 1/70; C12Q 1/68; C09K 11/00; B01D 57/02
[52] U.S. Cl. .................... 435/5; 435/6; 435/810; 536/23.1; 536/24.3; 536/24.32; 252/645; 204/601; 204/614
[58] Field of Search .................... 435/6, 810, 91.1; 536/24.3, 24.32, 23.1; 530/388.2; 935/1, 2, 8, 76, 77; 206/569; 204/180.1, 180.9, 182.3, 182.8; 252/645; 365/94, 120, 171

[56] References Cited

U.S. PATENT DOCUMENTS

| | | | |
|---|---|---|---|
| 4,234,683 | 11/1980 | McMillan | 435/18 |
| 4,252,897 | 2/1981 | Axford et al. | 435/34 |
| 4,283,489 | 8/1981 | Goodman et al. | 435/6 |
| 4,302,204 | 11/1981 | Wahl et al. | 23/230.3 |
| 4,358,535 | 11/1982 | Falkow et al. | 435/5 |
| 4,396,713 | 8/1983 | Simpson et al. | 435/6 |
| 4,526,865 | 7/1985 | Silman | 435/35 |
| 4,717,653 | 1/1988 | Webster, Jr. | 435/5 |
| 4,885,697 | 12/1989 | Hubner | 364/497 |
| 5,087,558 | 2/1992 | Webster, Jr. | 435/5 |

FOREIGN PATENT DOCUMENTS

| | | |
|---|---|---|
| 0076123 | 4/1983 | European Pat. Off. |
| 0155359 | 9/1985 | European Pat. Off. |
| 2823573 | 12/1978 | Germany |
| 2019408 | 10/1979 | United Kingdom |
| WO83/01073 | 3/1983 | WIPO |
| WO84/02721 | 7/1984 | WIPO |
| WO84/03716 | 9/1984 | WIPO |
| WO84/03715 | 9/1984 | WIPO |

OTHER PUBLICATIONS

Amikam et al., *Nucleic Acids Research*, 10(14): 4215–4272 (1982).
Fox et al., *International Journal of Systematic Bacteriology*, 27(1): 44–57 (Jan. 1977).
Tompkins et al., *The Journal of Infectious Diseases*, 141(5): 625–636 (May 1980).
Schmickel et al., *Am. J. Hum. Genet.*, 32: 890–897 (1980).
Nakamura et al. "Variable Number of Tandem Repeat (VNTR) Markers for Human Gene Mapping", *Science*, vol. 235, 27 Mar. 1987, pp. 1616–1622.
Sommer et al. "Minimal homology requirements for PCR primers", *Nucleic Acids Research*, vol. 17, No. 16, 1989, p. 6749.
Moore, "Nucleic Acid Reassociation as a Guide to Genetic Relatedness among Bacteria", *Current Topics*, vol. 64, 1974, pp. 105–128.
Altwegg, M. et al., Bacterial Molecular Epidemiology Based On A Non–Radioactive Probe Complementary To Ribosomal RNA, *Res. Microbiol.* 140:325–333 (1989).
Altwegg, M. et al., Ribosomal RNA Gene Restriction Patterns Provide Increased Sensitivity for Typing *Salmonella Typhi* Strains, *J. Infect. Dis.* 160(1):145–149 (Jul. 1989).
*Bergey's Manual of Systematic Bateriology*, vol. 1:279–288, (1974).
Buchanan, R.E., A Focus On The Meaning Of Bacterial Species, *International Bulletin of Bacteriological Nomenclature and Taxonomy* 15(1):25–32 (Jan. 15, 1965).
Callihan, D.R. et al., Ribosomal RNA gene polymorphism for identification of the *Bacteroides fragilis* group, Abstract submitted for the Annual Meeting of the American Society for Microbiology, Anaheim, California (May 13–17, 1990).
Davis, R.W. et al., *A Manual for Genetic Engineering, Advanced Bacterial Genetics*, Cold Spring Harbor Laboratory, Cold Spring Harbor, New York, pp. 120–121 (1980).
Degorce–Dumas, S.R. et al., Hybridization Between Mycoplasma DNAs, *Methods in Mycroplasmology* 1:319–325 (1983).
Delseny et al., Restriction Analysis of Radish Nuclear Genes Coding For rRNA: Evidence For Heterogeneity, *Biochemical and Biophysical Research Communications* 91(2):540–547 (1979).
Doi et al., Heterogeneity of the conserved ribosomal ribounucleic acid sequences of *Bacillus subtilis*, *J. Bacteriol.* 92(1):88–96 (Jul. 1966).
Drohan, W. et al., The Use Of Standard And Relaxed Hybridization Conditions To Detect Two Classes Of Sequences Related To Type–D Retroviruses In The DNAs Of Primates, *Biochim. et Biophys. Acta* 521:1–15 (1978).

(List continued on next page.)

*Primary Examiner*—W. Gary Jones
*Assistant Examiner*—Bradley L. Sisson
*Attorney, Agent, or Firm*—Sterne, Kessler, Goldstein & Fox

[57] ABSTRACT

A method of characterizing an unknown organism species which comprises, determining the position of part or whole of evolutionarily conserved DNA sequences in DNA of the organism, relative to the position of restriction endonuclease cleavage sites in the DNA, thereby to obtain an identifying genetic characterization of the unknown organism, and comparing the characterization with information from at least two sets of identifying genetic characterizations derived from the same conserved sequences, each of the sets defining a known organism species.

11 Claims, 16 Drawing Sheets

OTHER PUBLICATIONS

Geever, R.F. et al., Direct identification of sickle cell anemia by blot hybridization, *Proc. Natl. Acad. Sci. USA* 78(8):5081–5085 (Aug. 1981).

Gen–Probe Brochure: "Mycoplasma T.C. Detection Kit".

Goebel et al., Use of cloned mycoplasma ribosomal genes for detection of mycoplasma contamination in tissue cultures, *Abstracts of the Annual Meeting*, G23 (1984).

Gordon et al., *Bacillus subtilis, in Agriculture Handbook* No. 427, Agricultural Research Service, U.S. Department of Agriculture, Washington, D.C., pp. 36–41.

Hennecke, H., Recombinant plasmids carrying nitrogen fixation genes from *Rhizobium japonicum*, *Nature* 291:354–355 (May 28, 1981).

Hinojosa, M. et al., Use of Ribotyping Patterns in an Epidemiologic Study of *Shigella sonnei*, *Abstracts of the Annual Meeting of the American Society for Microbiology*, Abstract No. C–323 (1989).

Hugh, R. et al., Pseudomonas, *Manual of Clinical Microbiology*, 2nd Edition, American Society for Microbiology, Washington, D.C., pp. 250–269 (1974).

Kan, Y.W. et al., Polymorphism of DNA sequence adjacent to human β–globin structural gene: Relationship to sickle mutation, *Proc. Natl. Acad. Sci. USA* 75(11):5631–5635 (Nov. 1978).

Kiehlbauch, J.A. et al., Ribotyping of *Campylobacter*, *Abstracts of the Annual Meeting of the American Society for Microbiology*, p. 111, Abstract No. D–173 (1989).

LeGoff et al., Biologie Moleculaire, *C.R. Acad. Sc. Paris* t288:147–150 (Jan. 8, 1979).

Lerman, L.S. et al., Genetic Transformation I. Cellular Incorporation Of DNA Accompanying Transformation In *Pneumococcus*, *Biochim. et Biophys. Acta* 26:68–82 (1957).

Mao, S. et al., Ribotypes of *Legionella pneumophila* serogroup I, *Abstracts of the Annual Meeting of the American Society for Microbiology*, p. 113, Abstract No. D–183 (1989).

Martinetti, G. et al., rRNA Gene Restriction Patterns And Plasmid Analysis As A Tool For Typing *Salmonella enteritidis*, *Res. Microbiol.* 141:1151–1162 (1990).

Miyata, T. et al., Nucleotide sequence divergence and functional constraint in mRNA evolution, *Proc. Natl. Acad. Sci. USA* 77(12):7328–7332 (Dec. 1980).

Miyata, T. et al., Rapidly evolving mouseα–globin–related pseudo gene and its evolutionary history, *Proc. Natl. Acad. Sci. USA* 78(1):450–453 (Jan. 1981).

Moore et al., Comparative study of ribosomal ribounucleic acid cistrons in enterobacteria and myxobacteria, *J. Bacteriol.* 94(4):1066–1074 (Oct. 1967).

Mordarski et al., Ribosomal ribonucleic acid similarities in the classification of *Rhodococcus* and related taxa, *J. Gen. Microbiol.* 118:313–319 (1980).

Perry, R.P. et al., Persistent Synthesis of 5S RNA when Production of 28S and 18S Ribososmal RNA Is Inhibited by Low Doses of Actinomycin D, *J. Cell. Physiol.* 72:235–245 (1968).

Potter, S.S. et al., Specific cleavage analysis of mammalian mitochondrial DNA, *Proc. Natl. Acad. Sci. USA* 72:4496–4500 (Nov. 1975).

Razin et al., Detection of mycoplasmas infecting cell cultures by DNA hybridization, *In Vitro* 20(5):404–408 (May 1984).

Schaup, H.W., A Paradigm for Ribosome Fidelity Modulation in Protein Synthesis, *J. Theoret. Biol.* 70:215–224 (1978).

Seki, T. et al., Taxonomic Study of *Bacillus* by Deoxyribonucleic Acid–Deoxyribonucleic Acid Hybridization and Interspecific Transformation, *Int. J. Syst. Bacteriol.* 25(3):258–370 (Jul. 1975).

Sinclair et al., Retention of common nucleotide sequences in the ribosomal deoxyribonucleic acid of eukaryotes and some of their physical characteristics, *Biochemistry* 10:2761–2769 (1971).

Southern, E.M., Detection of Specific Sequences Among DNA Fragments Separated by Gel Electrophoresis, *J. Mol. Biol.* 98:503–517 (1975).

Stanier et al., The Differences Between Procaryotes and Eucaryotes: A Summing Up, *The Microbial World*, Fourth Edition, Prentic Hall, Inc., pp. 86–87 (1976).

Steinman, Specific Detection and Semiquantitation of Micro–Organisms in Tissue by Nucleic Acid Hybridization . . . , *J. Lab. Clin. Med.* 86:164–174 (1975).

Woese, Archaebacteria, *Scientific American* 244(6):98–122 (Jun. 1981).

Zuckerkandl, E. et al., Molecules as Documents of Evolutionary History, *J. Theoret. Biol.* 8:357–366 (1965).

Copy of opposition paper filed Feb. 24, 1994 by Zumstein & Klingseisen in corresponding European application No. 84301800.3 (EP Patent No. 0,120,658), together with uncertified English translation.

Rom, M., "Development of restriction fragment length polymorphism techniques in plants . . . ", *Thesis for the Degree of Master of Science*, Depart. of Genetics, The Hebrew Univ. of Jerusalem (May 1982) (certified English translation & declaration by Moshe Rom).

*Principles of Biochemistry*, 6th Edition, Eds. White et al., McGraw–Hill Book Col. "Genetic Aspect of Metabolism III", Chapter 27, pp. 860–881 (1978).

Copy of letter from Dr. M. Cohn to Dr. Bastian dated Nov. 1, 1993.

Rom, M. and Beckman, J., "Potential use of DNA polymorphism in breeding", *Bat–Sheva Seminar on Biological $N_2$–Fixation*, Rehovot, Israel, Sep. 1–9, 1981 (Abstract).

De Smedt & De Ley, "Intra– and Intergeneric Similarities of *Agrobacterium* Ribosomal Ribonucleic Acid Cistrons," *Int. J. Syst. Bacteriol.* 27:222–240 (Jul. 1977).

Findly & Gall, "Organization of ribosomal genes in *Paramecium tetraurelia*, " *J. Cell Biol.* 84:547–559 (Mar. 1980).

Martin, W. J., "Overview of Automation and Identification," *South Cent. Assoc. for Clin. Micro. News* 10:18–21 (1983).

Moseley et al., "Detection of Enterotoxigenic *Escherichia coli* by DNA Colony Hybridization," *J. Infect. Dis.* 142:892–898 (Dec. 1980).

Bohnert, H.J. et al., Homologies Among Ribosomal RNA and Messenger RNA Genes in Chloroplasts, Mitochondria and *E. Coli*, *Molec. gen. Genet.* 179:539–545 (1980).

De Ley, J. et al., Intra–and Intergeneric Similarities of *Chromobacterium* and *Janthinobacterium* Ribosomal Ribonucleic Acid Cistrons, *Int. J. Syst. Bacteriol.* 28(2):154–168 (Apr. 1978).

De Smedt, J. et al., Intra–and Intergeneric Similarities of Ribosomal Ribonucleic Acid Cistrons of Free–Living, Nitrogen–Fixing Bacteria, *Int. J. Syst. Bacteriol.* 30(1):106–122 (Jan. 1980).

Gillis, M. et al., Intra–and Intergeneric Similarities of the Ribosomal Ribonucleic Acid Cistrons of *Acetobacter and Gluconobacter, Int. J. Syst. Bacteriol.* 30(1):7–27 (Jan. 1980).

Malcolm, S. et al., A comparison of in situ hybridization techniques for gene localization, *Cytogenet. Cell Genet.* 19:256–261 (1977).

Swings, J. et al., *Frauteria,* a New Genus For "*Acetobacter aurantius*", *Int. J. Syt. Bacteriol.* 30(3):547–556 (Jul. 1980).

Botstein, D. et al., "Construction of a genetic linkage map in man using restriction fragment length polymorphisms", *Am. J. Hum. Genet.* 32:314–331 (1980).

Little, P.F.R. et al., "Model for antenatal diagnosis of β–thalassaemia and other monogenic disorders by molecular analysis of linked DNA polymorphisms", *Nature* 285:144–147 (May 15, (1980).

Miflin, B.J. et al., "The hordeins of barley: developmentally and nutritionally regulated multigene families of storage proteins", *Structure and Function of Plant Genomes,* pp. 1–8 (1983), Cifferri and Dure (Eds.), Plenum Press.

Rom, Moshe, "Development of restriction fragment length polymorphism techniques in plants as a tool for strain identification and breeding", *Thesis for the Degree of Master of Science, Department of Genetics—The Hebrew University of Jerusalem,* pp. 1–73 (May 1982), Beckmann and.

Amikam et al., Mycoplasmas (Mollicutes) Have a Low Number of rRNA Genes, *Journal of Bacteriology* 158(1):376–378 (1984).

Amikam et al., Ribosomal RNA genes in Mycoplasma, *Nucleic Acids Research* 10(14):4215–4222 (1982).

Arnheim et al., Molecular evidence for genetic exchanges among ribosomal genes on nonhomologous chromosomes in man and apes, *Proc. Natl. Acad. Sci. USA* 77(12):7323–7327 (1980).

Arnheim et al., Heterogeneity of the Ribosomal Genes in Mice and Men, *Cell* 11:363–370 (1977).

Arnot et al., Biochemical Identification of Cutaneous Leishmanias by Analysis of Kinetoplast DNA II. Sequence Homologies in Leishmania kDNA, *Molecular and Biochemical Parasitology* 3:47–56 (1981).

Atchison et al., Comparison of Chloroplast DNAs by Specific Fragmentation with EcoRI Endonuclease, *Molec. gen. Genet.* 148:263–269 (1976).

Bedbrook et al., Endonuclease recognition sites mapped on *Zea mays* chloroplast DNA, *Proc. Natl. Acad. Sci. USA* 73(12):4309–4313 (1976).

Beljanski et al., Particular Small Size RNA and RNA Fragments From Different Origins as Tumor Inducing Agents in *Datura stramonium, Molecular Biology Reports* 2:497–506 (1976).

Beljanski et al., Isolation of the Tumor–Inducing RNA from Oncogenic and Nononcogenic *Agrobacterium tumefaciens, Proc. Natl. Acad. Sci. USA* 71(5):1585–1589 (1974).

Beljanski et al., Decoupage des ARN ribosomiques d'*Escherichia coli* par la ribonuclease U et transcription in vitro . . . , *C.R. Acad. Sc. Paris* t286:1825–1828 (1978).

Bonen et al., Organization and expression of the mitochondrial genome of plants I. The genes for wheat mitochondrial ribosomal and transfer RNA . . . , *Nucleic Acids Research* 8(2):319–335 (1980).

Boros et al., Physical map of the seven ribosomal RNA genes of Escherichia coli, *Nucleic Acids Research* 6(5):1817–1830 (1979).

Brenner, D.J., Impact of Modern Taxonomy on Clinical Microbiology, *Amer. Soc. Microbio. News* 49(2):58–63 (19833).

Dunn et al., A Novel Method to Map Transcripts: Evidence for Homology between an Adenovirus mRNA and Discrete Multiple Regions of the Viral Genome, *Cell* 12:23–36 (1977).

Edwards et al., The rRNA operon from *Zea mays* chloroplasts: nucleotide sequence of 23s rDNA and its homology with *E. coli* rDNA, *Nucleic Acids Research* 9(12):2853–2869 (1981).

Fox et al., Comparative Cataloging of 16S Ribosomal Ribonucleic Acid: Molecular Approach to Procaryotic Systematics, *International Journal of Systematic Bacteriology* 27(1):44–57 (1977).

Fox et al., The Phylogeny of Prokaryotes, *Science* 209:457–463 (1980).

Gulati et al., Conditions for Using DNA Polymerase I as an RNA–Dependent DNA Polymerase, *Proc. Natl. Acad. Sci. USA* 71(4):1035–1039 (1974).

International Code of Nomenclature of Bacteria and [Selected] Statutes of the International Committee on Systematic Bacteriology . . . , Bacteriology Code, 1976 Revisions; ASM, Wash. D.C. (1975).

Kohne et al., Room Temperature Method for Increasing the Rate of DNA Reassociation by Many Thousandfold: The Phenol Emulsion Reassociation Technique, *Biochemistry* 16(24):5329–5341 (1977).

Krystal et al., Length Heterogeneity in a Region of the Human Ribosomal Gene Spacer is not Accompanied by Extensive Population Polymorphism, *J. Mol. Biol.* 126:91–104 (1978).

Krystal et al., Human nucleolus organizers on nonhomologous chromosomes can share the same ribosomal gene variants, *Proc. Natl. Acad. Sci. USA* 78(9):5744–5748 (1981).

Lamppa et al., Fine scale Interspersion of Conserved Sequences in the Pea and Corn Chloroplast Genomes, *Mol. Gen Genet.* 182:310–320 (1981).

MacKay et al., Nucleotide sequences of *Acanthamoeba castellanii* 5S and 5.8S ribosomal ribonucleic acids: phylogenetic and comparative structural analyses, *Nucleic Acids Res.* 9:3321–3334 (1981).

Martin, W.J., Overview of Automation and Identification, *South Cent. Assoc. for Clin. Micro. News* 10(2):18–21 (1983).

Mason et al., Molecular Probe for Identification of Medically Important Candida Species and *Torulopsis glabrata* 25(3):563–566 (1987).

Mattei et al., Biochemical Strain Characterization of *Trypanosoma cruzi* by Restriction Endonuclease Cleavage of Kinetoplast—DNA, *FEBS Letters* 74(2):264–268 (1977).

Mosely et al., Detection of Enterotoxigenic *Escherichia coli* by DNA Colony Hybridization, *J. Infect. Dis.* 142(6):892–898 (1980).

Moore, R.L., Nucleic Acid Reassociation as a Guide to Genetic Relatedness among Bacteria, in: Acore, R.U., *Curr. Topics in Microbiology and Immunobiology* 65:105–128 (1974).

Ostapchuk et al., Conserved Genes in Enteric Bacteria Are Not Identical, *Molec. gen. Genet.* 180:475–477 (1980).

Rochaix et al., Anatomy of the Chloroplast Ribosomal DNA of Chlamydomonas reinhardii, *Cell* 15:661–670 (1978).

Saillard et al., EcoRI Restriction Enzyme Analysis of Mycoplasma DNA, *Methods in Mycoplasmology* 1:313–318 (1983).

Sarin et al., Transcription of Heteropolymeric Regions of Avian Myeloblastosis Virus High Molecular Weight RNA with *Escherichia coli* DNA . . . I, *Biochem. and Biophys. Res. Comm.* 59(1):202–214 (1974).

Sawada et al., The Nuber of Ribosomal RNA Genes in *Mycoplasma capricolum, Mol. Gen. Genet.* 182:502–504 (1981).

Schmickel et al., HeLa Cell Indentification by Analysis of Ribosomal DNA Segment Patterns Generated by Endonuclease Restriction, *Am. J. Hum. Genet.* 32:890–897 (1980).

Shih et al., A General Method of Gene Isolation, *Proc. Natl. Acad. Sci. USA* 70(6):1697–1700 (1973).

Taylor et al., Efficient Transcription of RNA into DNA By Avian Sarcoma Virus Polymerase, *Biochimica et Biophysica Acta* 442:324–330 (1976).

Tompkins et al., Molecular Analysis of R–Factors from Multiresistant Nosocomial Isolates, *Journal of Infectious Diseases* 141(5):626–636 (1980).

Tu et al., Organization of rRNA structural genes in the archaebacterium *Thermoplasma acidophilum, Nucleic Acids Research* 10(22):7231–7245 (1982).

Uchida et al., The Use of Ribonuclease $U_2$ in RNA Sequence Determination, *J. Molec. Evolution* 3:63–77 (1974).

Van Etten et al., Precise Localization and Nucleotide Sequence of the Two Mouse Mitochondrial rRNA Genes and Three Immediately Adjacent Novel tRNA Genes, *Cell* 22:157–170 (1980).

Whitfeld et al., Mapping of the ribosomal RNA genes on spinach chloroplast DNA, *Nucleic Acids Res.* 5(6):1741–1751 (1978).

Woese et al., Secondary structure model for bacterial 16S ribosomal RNA: phylogenetic, enzymatic and chemical evidence, *Nucleic Acids Research* 8(10):2275–2293 (1980).

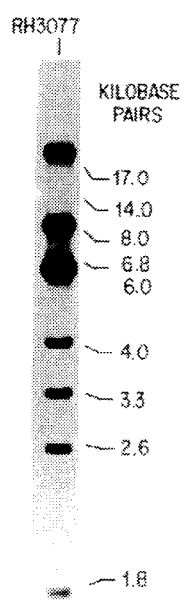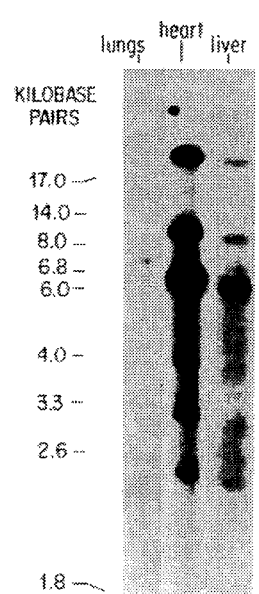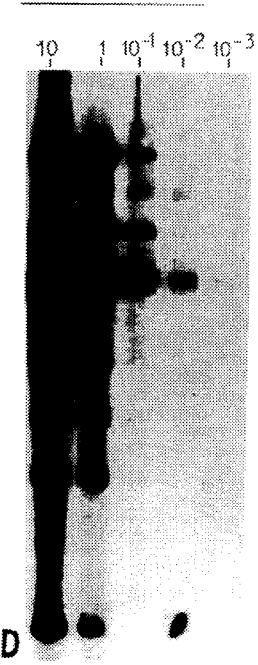
FIG.12A    FIG.12B    FIG.12C    FIG.12D

METHOD FOR IDENTIFYING AND CHARACTERIZING ORGANISMS

This application is a continuation of application Ser. No. 07/731,153, filed Jul. 15, 1991 now abandoned which is a division of application Ser. No. 07/294,903, filed Jan. 4, 1989, now U.S. Pat. No. 5,087,558, issued Feb. 11, 1992 which is a continuation of application Ser. No. 06/892,064 filed Aug. 1, 1986, abandoned, which is a continuation of application Ser. No. 06/477,431, filed Mar. 21, 1983 abandoned, which is a continuation-in-part of application Ser. No. 305,498, filed Sep. 25, 1981, now U.S. Pat. No. 4,717,653, issued Jan. 5, 1988.

FIELD OF THE INVENTION

The present invention relates to a method for the rapid and accurate characterization and identification of organisms, including prokaryotic and eukaryotic organisms, such as bacteria, plants, and animals.

BRIEF DESCRIPTION OF THE PRIOR ART

The classification of living organisms has traditionally been done along more or less arbitrary and somewhat artificial lines. For example, the living world has been divided into two kingdoms: Plantae (plants) and Animalia (animals). This classification works well for generally familiar organisms, but becomes difficult for such organisms as unicellular ones (e.g., green flagellates, bacteria, blue-green algae), since these differ in fundamental ways from the "plants" and "animals".

It has been suggested to simply divide organisms with respect to the internal architecture of the cell. In this scheme, all cellular organisms are either prokaryotic or eukaryotic. Prokaryotes are less complex than eukaryotes, they lack internal compartmentalization by unit membrane systems, and lack a defined nucleus. Prokaryotic genetic information is carried in the cytoplasm on double-stranded, circular DNA; no other DNA is present in cells (except for the possible presence of phage, bacterial viruses, and cirular DNA plasmids, capable of autonomous replication). Eukaryotes, on the other hand, have a multiplicity of unit membrane systems which serve to segregate many of the functional components into specialized and isolated regions. For example, genetic information (DNA) can be found in a well-compartmentalized nucleus and also in organelles: mitochondria and (in photosynthetic organisms) chloroplasts. The replication, transcription, and translation of the eukaryotic genome occurs at either two or three distinct sites within the cell: in the nucleocytoplasmic region, in the mitochondrion, and in the chloroplast.

The differences between prokaryotes and eukaryotes, however, breaks down when a comparison of mitochondria and chloroplasts is carried out with prokaryotes: these organelles are today considered to have been derived from free-living prokaryotes, which entered into an endosymbiotic relation with primitive eukaryotes, and eventually became closely integrated with the machinery of the host cell and incapable of independent existence (see e.g., Fox, G. E. et al, *Science* 209:457–463 (1980), at 462; Stanier, R. Y. et al, "The Microbial World," Fourth Edition, Prentice-Hall, Inc., 1976, at p. 86). For example, it has been demonstrated that DNA from mouse L cell mitochondria carrying the ribosomal RNA gene region exhibits notable sequence homologies to *Escherichia coli* ribosomal RNA, thus providing strong support for the endosymbiotic model (Van Etten, R. A. et al, *Cell*, 22:157–170 (1980)). It has also been shown that the nucleotide sequence of 23S ribosomal DNA from Zea mays chloroplast has 71% homology with 23S ribosomal DNA from *E. coli* (Edwards, K. and Kossel, H., *Nucleic Acids Research*, 9:2853–2869 (1981)); other related work (Bonen, L. and Gray, M. W., ibid, 8:319–335 (1980)) also further supports the general concept.

In this model the eukaryotic cell is a phylogenetic "chimera" with organelle components that are clearly prokaryotic in nature. The "prokaryotic-eukaryotic" dichotomy then, also has drawbacks, even as a broad classification method.

Where classification of organisms becomes more than a scientific exercise is in the identification of plants and animals for hybridization and breeding purposes, and in the accurate and reliable identification of microorganisms which may infect so-called "higher" organisms or other media. For example, the plant-breeder, cattle breeder, or fish breeder may wish to have a quick and reliable means of identifying different species and strains of their subjects. The veterinarian, physician, or horticulturist may wish to have an accurate identification of any infectious organisms (parasites, fungi, bacteria, etc.) and viruses present in examined plant or animal tissues. The correct identification of species of these organisms and viruses is of particular importance.

The problem can best be illustrated by referring to the identification of bacteria. Names of bacterial species usually represent many strains, and a strain is considered to be a population derived from a single cell. Bacterial species are usually defined by describing the degree of homogeneity and diversity of attributes in representative samples of strains of species. Precise definitions of bacterial species are difficult to express because subjective limits to strain diversity within species are required to define species boundaries. (Buchanan, R. E., *International Bulletin of Bacteriological Nomenclature and Taxonomy*, 15:25–32 (1965)). The practical application of definitions of species to the identification of an unknown bacterial strain requires the selection of relevant probes, such as substrates and conditions to detect phenotypic attributes, and radioactively-labeled DNA from the same species. Because of the diversity of bacterial species, a screening procedure is the primary tool used in the classical, progressive method for identification of a strain. Results of the screening procedure are then used to predict which other laboratory methods and reagents are relevant for definitive identification of the strain. Identification is ultimately based on certain phenotypic and genotypic similarities between the unidentified strain and characterized species. The challenge is to precisely define the boundaries of species, preferably in terms of a standard probe which reveals species-specific information, so that definitions of species can be directly and equally applied to the identification of unknown strains.

*Bergey's Manual of Determinative Bacteriology* (Buchanan, R. E. and Gibbons, N. E., Editors, 1974, 8th Edition, The Williams & Wilkins Company, Baltimore) provides the most comprehensive treatment of bacterial classification particularly for nomenclature, type strains, pertinent literature, and the like. It is, however, only a starting point for the identification of any species since, inter alia, it is normally out of date, and is limited in space to describing species quite briefly. (See for example, Brenner, D. J., "Manual of Clinical Microbiology," 3rd Edition, American Society of Microbiology, Washington, D.C., 1980, pages 1–6.)

The term "species", as applied to bacteria, has been defined as a distinct kind of organism, having certain distinguishing features, and as a group of organisms which generally bear a close resemblance to one another in the more essential features of their organization. The problem with these definitions is that they are subjective; Brenner, supra, at page 2. Species have also been defined solely on the basis of criteria such as host range, pathogenicity, ability or inability to produce gas in the fermentation of a given sugar, and rapid or delayed fermentation of sugars.

In the 1960's, numerical bacterial taxonomy (also called computer or phenetic taxonomy) became widely used. Numerical taxonomy is based on an examination of as much of the organism's genetic potential as possible. By classifying on the basis of a large number of characteristics, it is possible to form groups of strains with a stated degree of similarity and consider them species. Tests which are valuable for the characterization of one species, however, may not be useful for the next, so this means to define species is not directly and practically applicable to the identification of unknown strains. Although this may be overcome in part by selecting attributes which seem to be species specific, when these attributes are used to identify unknown strains, the species definition is applied indirectly. See for example Brenner, supra, at pages 2-6. The general method, furthermore, suffers from several problems when it is used as the sole basis for defining a species, among them the number and nature of the tests to be used, whether the tests should be weighted and how, what level of similarity should be chosen to reflect relatedness, whether the same level of similarities is applicable to all groups, etc.

Hugh, R. H. and Giliardi, G. L., "Manual of Clinical Microbiology," 2nd Edition, American Society for Microbiology, Washington, D.C., 1974, pages 250–269, list minimal phenotypic characters as a means to define bacterial species that makes use of fractions of genomes. By studying a large, randomly selected sample of strains of a species, the attributes most highly conserved or common to a vast majority of the strains can be selected to define the species. The use of minimal characters is progressive and begins with a screening procedure to presumptively identify a strain, so that the appropriate additional media can be selected. Then the known conserved attributes of the species are studied with the expectation that the strain will have most of the minimal characters. Some of the minimal characters do not occur in all strains of the species. A related concept is the comparative study of the type, the neo-type, or a recognized reference strain of the species. This control is necessary because media and procedures may differ among laboratories, and it is the strain, not the procedure, that is the standard for the species.

A molecular approach to bacterial classification is to compare two genomes by DNA—DNA reassociation. A genetic definition of species includes the provision that strains of species are 70% or more related. With DNA—DNA reassociation a strain can be identified only if the radioactively labeled DNA probe and unknown DNA are from the same species. The practical application of this 70% species definition however is limited by selection of an appropriate probe. This may be overcome in part by selecting phenotypic attributes which seem to correlate with the reassociation group, but when these are used alone the DNA—DNA reassociation species definition is also applied indirectly.

Brenner, supra, at page 3, states that the ideal means of identifying bacterial species would be a 'black box' which would separate genes, and instantly compare the nucleic acid sequences in a given strain with a standard pattern for every known species—something akin to mass spectrophotometric analysis.

Brenner, however, concedes that although restriction endonuclease analysis can be done to determine common sequences in isolated genes, "we are not at all close to having an appropriate black box, especially one suited for clinical laboratory use." His words could be equally applied to any species of organism.

This brief review of the prior art leads to the conclusion that there presently exists a need for a rapid, accurate, and reliable means for identifying unknown bacteria and other organisms, and to quickly classify the same, especially to identify the organism of a disease, or of a desirable biochemical reaction. The method should be generally and readily useful in clinical laboratories, should not be dependent on the number of tests done, on the subject prejudices of the clinician, nor the fortuitous or unfortuitous trial and error methods of the past. Further, a need also exists for a method useful for identifying and distinguishing genera and species of any living organism, which can be readily and reliably used by veterinarians, plant-breeders, toxicologists, animal breeders, entomologists and in other related areas, where such identification is necessary.

SUMMARY OF THE INVENTION

It is therefore an object of the invention to provide a quick, reliable and accurate method of objectively identifying organisms, especially—but not limited to—microorganisms.

Yet another object of the invention is to provide a method of identifying organisms such as bacteria which utilizes the organisms' genome.

Another object of the invention is to provide a method of characterizing and identifying species and genera of pathogenic organisms in the clinical laboratory, so as to provide the capability of characterizing and identifying the cause of any given animal or plant disease.

Still another object of the invention is to provide various products useful in the aforementioned methodologies.

These and other objects of the invention, as will hereinafter become more readily apparent, have been attained by providing:

A method of characterizing an unknown organism species which comprises determining the position of part or whole of evolutionarily conserved sequences in the DNA of said organism, relative to the position of restriction endonuclease cleavage sites in said DNA, thereby to obtain an identifying genetic characterization of said unknown organism, and comparing said characterization with information from at least two sets of identifying genetic characterizations derived from the same conserved sequences, each of said sets defining a known organism species.

Still another object of the invention has been attained by providing:

A method of diagnosing a pathogenic organism infection in a sample which comprises identifying the organism in said sample by the aforementioned method.

BRIEF DESCRIPTION OF THE DRAWINGS

FIG. 12 shows the detection of *Streptococcus pneumoniae* in EcoR I digested DNA from infected mouse tissues using cDNA from 16S and 23S rRNA from *E. coli* as the probe.

DETAILED DESCRIPTION OF THE PREFERRED EMBODIMENTS

Figure 1:
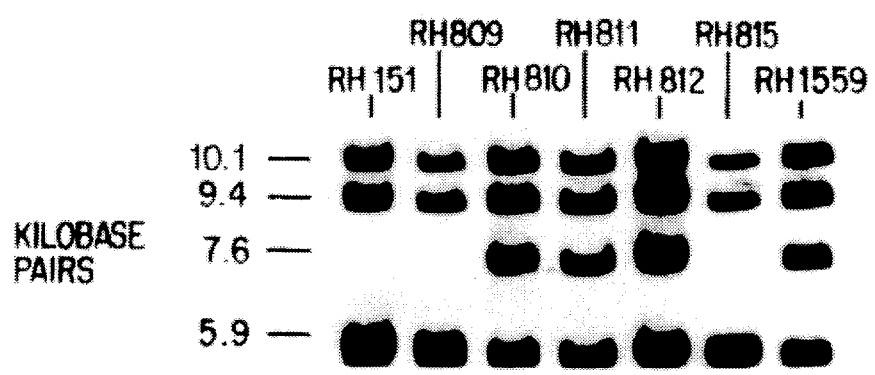
FIG. 1 shows the EcoR I restriction endonuclease digest of DNA isolated from strains of *Pseudomonas aeruginosa*, using cDNA to 16S and 23S ribosomal RNA (rRNA) of *E. coli* as the probe.

This invention is based on the inventor's realization that, if species are discrete clusters of strains related to a common speciation event, there should be, despite divergence, a likeness shared by strains that objectively defines the species boundary; strains of species should contain structural information which is a clue to their common origin. The greatest amount of an organism's past history survives in semantides, DNA and RNA, (Zuckerkandle, E. and Pauling, L., *Journal of Theoretical Biology*, 8:357–366 (1965)).

In U.S. Pat. No. 4,717,653, (herein incorporated by reference) the inventor described a system for the definition of species and characterization of organisms which makes use of information contained in ribosomal RNA genes (rRNA). Ribosomal RNA has a structural and functional role in protein synthesis (Schaup, *Journal of Theoretical Biology*, 70:215–224 (1978)), and the general conclusion from rRNA-DNA hybridization studies, is that the base sequences of ribosomal RNA genes are less likely to change, or are more conserved during evolution, than are the majority of other genes (Moore, R. L., *Current Topics In Microbiology and Immunobiology*, Vol. 64:105–128 (1974), Springer-Verlag, New York). For example, the primary structure of 16S rRNA from a number of bacterial species has been inferred from oligonucleotide analysis (Fox, G. E. et al, *International Journal of Systematic Bacteriology*, 27:44–57 (1977)). There are negligible differences in the 16S oligomer catalogs of several strains of *E. coli* (Uchida, T. et al, *Journal of Molecular Evolution*, 3:63–77 (1974)); the substantial differences among species, however, can be used for a scheme of bacterial phylogeny (Fox, G. E., *Science*, 209:457–463 (1980)). Different strains of a bacterial species are not necessarily identical; restriction enzyme maps show that different EcoR I sites occur in rRNA genes in two strains of *E. coli* (Boros, I. A. et al, *Nucleic Acids Research* 6:1817–1830 (1979)). Bacteria appear to share conserved rRNA gene sequences and the other sequences are variable (Fox, 1977, supra).

The present inventor had thus discovered that restriction endonuclease digests of DNA have sets of fragments containing conserved sequences that are similar in strains of a species of organism (e.g., bacteria), but different in strains of other species of the organism; i.e., despite strain variation, enzyme specific sets of restriction fragments with high frequencies of occurrence, minimal genotypic characters, define the species. This is the essence of the invention described by U.S. Pat. No. 4,717,653, and also that of the invention described herein.

The present invention constitutes an extension of the concepts developed in U.S. Pat. No. 4,717,653, in that it has further been discovered that there exist sequences, in addition to those of rRNA, which are highly conserved through evolution and which may be as useful as rRNA sequences in the identification system. In other words, the present invention provides means for carrying out the identification and characterization techniques of U.S. Pat. No. 4,717,653 using any probe which is conserved, rRNA being just one example. The present invention also provides additional examples of methods which may be used in the identification process. The present inventor has also discovered that the method is general, in that it is applicable to both eukaryotic and prokaryotic DNA, using a conserved nucleic acid probe from any organism, prokaryotic or eukaryotic, of the same or different (classic) taxonomic classification than the organism being identified.

The invention offers an objective method of defining organisms based on conserved DNA sequences in relation to restriction endonuclease sites. The detection of restriction fragments containing a conserved sequence may be carried out by hybridizing or reassociating DNA segments with nucleic acid containing conserved sequence information from a probe organism.

By the "organism" which can be characterized (which term is meant to include "identified") by the process of the invention, it is meant to include virtually any organism which, by definition, contains DNA. In this respect it is useful to refer to a classical taxonomic scheme as a point of reference.

All organisms belonging to the Kingdoms Monera, Plantae and Animalia are included. For example, among those of the Kingdom Monera can be mentioned the Schizomycetes (Bacteria) of the classes myxobacteria, spirochetes, eubacteria, rickettsiae, and the cyanopytha (blue green algae). Among those of the Kingdom Plantae can be mentioned the Division Euglenophyta (Euglenoids), Division Chlorophyta (green-algae) classes chlorophyceae and charophyceae, Division Chrysophyta, classes xanthophyceae; chrysophyseae, bacillariophyceae; Division Pyrrophyta (Dinoflagellates); Division Phaeophyta (Brown algae); Division Rhodophta (Red algae); Division Myxomycophyta (slime molds), classes myxomycetes, acrasiae, plasmodiophoreae, labyrinthuleae; Division Eumycophyta (true fungi), classes phycomycetes, ascomycetes, and basidomycetes; Division Bryophta, classes hepaticae, anthocerotae, and musci; Division Tracheophyta (Vascular plants), subdivisions psilopsida, lycopsyda, sphenopsida, pteropsida, spermopsida classes cycadae, ginkgoae, coniferae, gneteae and angiospermae subclasses dicotyledoneae, monocotyloedoneae. Among those of the Kingdom Animalia can be mentioned the Subkingdom Protozoa, Phylum Protozoa (Acellular animals) subphylum plasmodroma, classes flagellata, sarcodina and sporozoa; subphylum ciliophora, class ciliata; the Subkingdom Parazoa, Phylum porifera (Sponges), class calcarea, hexactinellida, and desmospongiae; the Subkingdom Mesozoa, Phylum mesozoa; the Subkingdom Metazoa, Section Radiata, Phylum coelenterata, classes hydrozoa, scyphozoa, anthozoa, Phylum ctenophora, classes tentaculata and nuda; Section Protostomia Phylum platyhelmintes (flat-worms) classes tubeliana, trematoda, and cestoda; Phylum nemertina; Phylum acanthocephala; Phylum aschelmintles, classes rotifera, gastrotricha, kinorhyncha, priapulida, nematoda and nematomorpha; Phylum entoprocta; Phylum ectoprocta, classes gymnolaemata and phylactolaemata; Phylum phoronida; Phylum braciopoda, classes inarticulata and articulata; Phylum mollusca (molluscs) classes amphineura, monoplacophora, gastropoda, scaphopoda, pelecypoda, and cephalopoda; Phylum sipunculida; Phylum echiurida; Phylum annelida, classes polychaeta, oligochaeta and hirudinea; Phylum onychophora; Phylum tardigrada; Phylum pentastomida; Phylum arthropoda, subphylum trylobita, subphylum chelicerata classes xiphosura, arachmida, pycnogomida, subphylum mandibulata classes crustacea, chilopoda, diplopoda, pauropoda, symphyla, insecta of the orders collembola, protura, diplura, thysanura, ephemerida, odonata, orthoptera, dermaptera, embiania, plecoptera, zoraptera, corrodentia, mallophaga, anoplura, thysasnoptera, hemiptera, neuroptera, coleoptera, hymenoptera, mecoptera, siphonaptera, diptera, trichoptera and lepidoptera; those of the Section Deuterostomia, phylum chaetognatha, phylum echinodermata, classes crinoidea, asterordea, ophiuroidea, echinoidea, and holoturoidea, phylum pogonophora; phylum hemichordata, classes enteropneusta, and pterobranchia; phylum chordata, subphylum urochordata, classes ascidiaciae, thaliaceae, larvacea; subphylum cephalochordata, subphylum vertebrata, classes agnatha, chondrichthyes, osteichthyes (subclass saccopteiygii orders crossopterygii and dipnoi), amphibia, repitilia, aves and mammalia, subclass prototheria, subclass theria, orders marsupialia, insectivora, dermoptera, chiroptera, primates, edentata, pholidota, lagomorpha, rodentia, cetaceae, carnivora, tubulidentata, probosicdea, hyracoidea, sirenia, perissodactyla and artiodactyla.

It is understood that beyond the order, the organisms are still classified according to their families, tribes, genus and species, and even subspecies, infra-subspecific taxons, and strains or individuals. In addition, cell cultures (plant or animal), as well as viruses can also be identified. These classifications are used in this application for illustrative purposes only, and are not to be taken as exclusive. The organism is either known or unknown, most commonly the organism is an unknown being identified.

Functionally, for the purposes of this invention, it is convenient to divide all organisms into the eukaryotes and the prokaryotes. When identifying a prokaryotic organism, the DNA to be analyzed is that present in the cells or in the non-compartmentalized chromosomes. When identifying a eukaryotic organism one may either use the nuclear DNA or the organelle DNA (mitochondrial DNA or chloroplast DNA).

Briefly, high molecular weight DNA and/or small circular DNAs are isolated from the organism to be identified in order to analyze the conserved sequences (and possibly sequences that could be used to create a taxon below the rank of species or infrasubspecific subdivisions.) The DNA's are extracted by methods which are well-known to the art.

The DNA's are analyzed to ascertain both 1) the presence and position of the conserved sequences and 2) their position relative to endonuclease restriction sites. The easiest way to analyze for the presence of the conserved sequences is to utilize a polynucleotide probe capable of hybridizing with the conserved DNA sequence. However, direct sequence information as obtained by chemical sequence determination and analysis thereof could also be utilized. In U.S. Pat. No. 4,717,653 the probe utilized was an rRNA information containing-probe; in this case any probe having conserved sequences could be used. In an analogous manner, the easiest way of finding a given set of endonuclease restriction sites is to cleave the DNA with the appropriate restriction enzymes. (This, indeed, is the manner taught and practiced in U.S. Pat. No. 4,717,653). However, alternative methods, such as sequence information coupled with known restriction site sequences, or cleavage and partial sequencing could also be used.

Most commonly DNA's are going to be cut at specific sites into fragments by restriction endonucleases. The fragments are separated according to size by a chromatographic system. In U.S. Pat. No. 4,717,653 gel chromatography was used as an example of a useful chromatographic system. However, other systems can also be used, such as high pressure liquid chromatography, capillary zone electrophoresis, or other separation techniques. In using gel chromatography, the fragments are separated, the gels are stained, as is otherwise well-known in the art, and standardized as to the fragment sizes using standards curves constructed with fragments of known sizes. The separated fragments may then be transferred to cellulose nitrite paper by the Southern blot technique (Southern, E. M., *Journal of Molecular Biology,* 38:503–517 (1975), herein incorporated by reference), and covalently bound thereto by heating. The fragments containing the conserved sequences are then located by their capacity to hybridize with a nucleic acid probe containing conserved sequence information. Alternatively, hybridization can occur after digestion but before separation; or restriction cleavage can occur after hybridization, followed by separation of the fragments.

The nucleic acid probe can either be non-radioactively labeled or, preferably, radioactively labeled. When radioactively labeled, the probe can be RNA, or preferably DNA which is complementary to RNA (cDNA), either synthesized by reverse transcription or contained on a cloned fragment, which can be labeled, for example, by nick translation. Also, synthetic oligodeoxyribonucleotides may be prepared with labeled nucleotides.

The well-defined probe is derived from an arbitrarily chosen organism, see infra, or may be a consensus sequence. Once hybridization has occurred, the hybridized fragments are detected by selectively detecting double stranded nucleic acid (non-radiolabeled probe), or visualized by, e.g., autoradiography (radiolabeled probe). The size of each fragment which has been hybridized is relative to the restriction sites and is determined from the distance traveled using standard curves, as described previously. The amount of hybridization, the pattern of hybridization, and the sizes of the hybridized fragments, which are relative to restriction sites, can be used individually or in conjunction to identify the organism.

The genetic characterization that emerges from this technique can be readily compared to equivalent characterizations derived from at least two and up to a multiplicity of known, standard organisms, genera or species. After a preliminary broad classification has already been carried out (using, for example, classical taxonomy), the comparison can be either by visual inspection and matching of appropriate chromatographic patterns, (as in U.S. Pat. No. 4,717, 653) by comparison of hybridized restriction fragment sizes, by band intensity (amount of hybridization) or by any combination thereof. Ideally, the comparison is carried out with a one-dimensional computer-based pattern recognition system, such as those used in point-of-sale transactions.

The present inventor discovered that when using the aforementioned method, the genetic characterizations for organisms of the same species are substantially similar, with minor variations allowed for intraspecies differences due to strain variations, whereas differences between species, and differences between genera (and higher classifications) are maximal.

The use of enzyme-specific fragment variations among strains of a species permits the typing of strains for various purposes; e.g. in the case of bacteria, for epidemiological purposes. In fact, restriction enzymes can be chosen for their ability to distinguish strains within species.

The "probe organism" used in the present invention, and from which is obtained the nucleic acid probe, can also be any of the aforementioned organisms; it can be either eukaryotic or prokaryotic. The only limitation is given by the fact that the conserved sequence-containing probe should hybridize maximally with the unknown organism's DNA.

There are four types of conserved sequence information-containing probes: 1) prokaryotic probes (especially bacterial-derived ), 2) eukaryotic mitochondrial probes, 3) eukaryotic chloroplast probes, and 4) eukaryotic non-organelle probes. There are also four sources of DNA (to be endonuclease digested): 1) prokaryotic cellular DNA, 2) eukaryotic mitochondrial DNA, 3) eukaryotic chloroplast DNA, and 4) eukaryotic nuclear DNA. The following hybridization table can thus be constructed ( Table 1 ).

TABLE 1

Hybridization Table

| Unknown organism DNA | Conserved Gene Sequence Probe | | | |
|---|---|---|---|---|
| | Pro-karyotic | Eukaryotic | | |
| | | Mito-chondrial | Chloro plast | Non-organelle |
| Prokaryotic | + | + | + | − |
| Eu.[1] Mitochondria | + | + | + | − |
| Eu. Chloroplast | + | + | + | − |
| Eu. Nuclear | −[2] | − | − | + |

[1]Eu = Eukaryotic
[2]= refers to generally less effective hybridization, see Example 4, infra.

The Table shows which probes can generally be maximally hybridized with which unknown DNA. For example, one can identify a eukaryotic organism by extracting species specific mitochondrial or chloroplast DNA, endonuclease-digesting it and hybridizing the digest with either a prokaryotic probe, or with an organelle derived eukaryotic probe. In the same manner, one can identify a prokaryotic organism by extracting species-specific cellular DNA, endonuclease-digesting it, and hybridizing the digest with either a prokaryotic probe, or an organelle-derived eukaryotic RNA probe. Also, one can identify a eukaryotic organism by extracting and digesting species-specific nuclear DNA, and hybridizing it with a non-organelle derived eukaryotic probe. Eukaryotes could be defined by one or any combination of the nuclear, mitochondria, or in some cases chloroplast systems. These cross-hybridizations are based on the fact that nucleic acid derived from eukaryotic organelles has extensive homology with evolutionarily conserved sequences from prokaryotic nucleic acid, but that the same homologies are generally not present to such extent between nuclear-derived eukaryotic DNA and prokaryotic DNA.

The choice of any pair of DNA to be digested and accompanying probe is arbitrary, and will depend on the organism being identified, i.e. it will depend on the question asked. For example, in detecting a prokaryotic species (e.g. bacteria) present in or together with a eukaryotic cell (e.g. animal or plant) for purposes of detecting and identifying an infecting agent, one may choose a prokaryotic probe and work under conditions where organelle-derived DNA is not extracted or only minimally extracted. In this manner one assures that interference between organelle-derived DNA and prokaryotic DNA is minimal. In identifying a eukaryotic species (which is not infected with a prokaryote) with a prokaryotic probe, it is best to maximize the concentration of organelle-derived DNA, as for example by separating organelles from nuclei, and then extracting only organelle DNA. If one wishes to identify a eukaryotic organism which has been infected with a prokaryotic organism, it is best to use a non-organelle, non-prokaryotic derived probe since it will generally not hybridize well with the DNA from the prokaryote.

It is preferred to use a pair (DNA and probe) from the same kingdom, or same subkingdom, or same section, or same phylum, or same subphylum, or same class, or same subclass, or same order, or same family or same tribe or same genus. It is particularly preferred to use prokaryotic probe (e.g. bacterial probe) to hybridize with prokaryotic DNA. In this manner one could detect, quantify, and identify genera, species, and strains of prokaryotic organisms. One of the most preferred prokaryotic probes is derived from bacteria, and further, because of the ease and availability, from *E. coli*. The probe from *E. coli* can be used to identify any organism, especially any prokaryotic organism, most preferably a strain of any bacterial species. Another particularly preferred embodiment is to use eukaryotic probe derived from a given class to identify eukaryotic organisms of the same class (e.g. mammalian probe to identify mammalian organism). Most preferred is to use probe and DNA from the same subclass and/or order and/or family of organisms, (e.g. if identifying a species of mouse, it is preferred to use mouse-derived probe).

The most sensitive and useful pair systems are those where there is less evolutionary distance or diversity between the source of the probe and the unknown DNA.

The phrase "evolutionarily conserved DNA sequence" is used in this invention to denote DNA sequences that show homology between at least two different species of plants, animals or microorganisms. The homology between two conserved sequences is to be such that, if one of said DNA molecules were to be detectably labeled, sufficient hybridization or annealing would occur if both single stranded DNA molecules or fragments thereof were placed together under hybridization conditions, thereby to produce a duplex of sufficient stability to be detectable by standard methodology (i.e., radiolabelling, enzyme labelling, and the like).

In U.S. Pat. No. 4,717,653 the evolutionarily conserved sequence exemplified was that of ribosomal RNA genes. This is still a highly preferred gene sequence. However, it has been discovered that other gene sequences exist which are sufficiently conserved across the evolutionary span to be useful.

Examples of such additional sequences are those of genes or portions thereof coding for transfer RNA, or proteins denoted as belonging to the same Superfamily, or same Family, preferably same Subfamily or even same entry in Dayhoff's "Atlas of Protein Sequence and Structure", Volume 5, Supplement 3, 1978, NBR, 1979, pages 9–24, herein incorporated by reference. A Family of proteins is one wherein any two proteins differ from each other by less than 50% amino acid residues in their sequence. A Subfamily of proteins is one wherein any two proteins differ from each other by less than 20% amino acid residues in their sequence. An "Entry" is one wherein any two proteins differ from each other by less than 5% amino acid residues in their sequence.

Specific examples of gene sequences or appropriate portions thereof which can be used are: cytochrome C related genes, cytochrome $C_3$ related genes, cytochrome $c_1$ related, cytochrome $b_5$ related, ferrodoxin related, rebredoxin related, flavodoxin related, alcohol dehydrogenase related, lactate drhydrogenase related, peroxidase related, adenylate kinase related, phospholipase $A_2$ related, tryptophan operon related, carboxypeptidase related, subtilisin related, penicillinase related, protease inhibitor related, somatotropin related, corticotropin related, lipotropin related, glucagon related, snake venom toxin related, plant toxin related, antibacterial toxin related, immunoglogulin related gene, ribosomal other than rRNA-related genes, heme carrier genes, chromosomal protein genes, fibrous protein genes, and the like.

The conservation of some of these additional DNA sequences is not as widespread throughout the animal, plant or microbiological domains as is that of the rRNA genes. (Thus the still preferred use of rRNA). This, however, does not constitute a serious impediment to their use since it may be possible to utilize such additional sequences to identify or characterize organisms within more limited ranges or subdomains. For example it may be possible to utilize trp D gene sequences from bacteria to generate a trp D bacterial probe and then use this probe to test within the bacterial domain. In fact, it may be possible to use a trp D probe within an even narrower domain (e.g., test for the presence of Enterobacteriaceae, or of Bacillus, etc.) with a trp D probe from the same order, family or genus. Thus, while the range of applicability of some of the additional probe sequences may not be as broad as that of rRNA probes, their applicability will nevertheless be quite effective within narrower domains.

A probe containing the conserved DNA sequence information is prepared in the same manner as the preparation of rRNA information containing probe exemplified in U.S. Pat. No. 4,717,653. The probe can thus be RNA, DNA or cDNA, and the like.

The individual steps involved in the technique will be described hereinafter broadly with reference to both eukaryotic and prokaryotic cells when applicable, or specifically for each type of cell if some difference in technique exists.

The first step is extraction of the DNA from the unknown organisms. Nuclear DNA from eukaryotic cells can be selectively extracted by standard methodology well-known to the art (see for example, Drohan, W. et al, *Biochem. Biophys. Acta*, 521 (1978), 1–15, herein incorporated by reference). Because organelle DNA is small and circular, spooling techniques serve to separate the non-circular nuclear DNA from the circular, organelle-derived DNA. As a corollary, the non-spooled material contains the organelle-derived DNA which can separately be isolated by density gradient centrifugation. Alternatively, mitochondria (or chloroplasts) are separated from a mixture of disrupted cells; the purified mitochondrial (or chloroplast) fraction is used for the preparation of organelle-derived DNA while the purified nuclear fraction is used to prepare nuclear DNA. (See for example Bonen L. and Gray, M. W., *Nucleic Acids Research*, 8:319–335 (1980)).

Prokaryotic DNA extraction is also well-known in the art. Thus, for example, an unknown bacterium present in any medium, such as an industrial fermentation suspension, agar medium, plant or animal tissue or sample or the like, is treated under well-known conditions designed to extract high molecular weight DNA therefrom. For example, cells of the unknown organism can be suspended in extraction buffer, lysozyme added thereto, and the suspension incubated. Cell disruption can be further accelerated by addition of detergents, and/or by increase in temperature. Protease digestion followed by chloroform/phenol extraction and ethanol precipitation can be used to finalize the extraction of DNA. An alternative method of extraction, which is much faster than phenol/chloroform extraction, is rapid isolation of DNA using ethanol precipitation. This method is preferably used to isolate DNA directly from colonies or small, liquid cultures. The method is described in Davis, R. W. et al: "A Manual for Genetic Engineering, Advanced Bacterial Genetics," (hereinafter "Davis"), Cold Spring Harbor Laboratory, Cold Spring Harbor, N.Y., 1980, pp. 120–121, herein incorporated by reference.

The DNA (prokaryotic or eukaryotic (nuclear or non-nuclear)) is dissolved in physiological buffer for the next step. There are a variety of possible steps to be followed after isolation of the desired DNA. One of these steps is endonuclease digestion.

Digestion of extracted DNA is carried out with restriction endonuclease enzymes. Any restriction endonuclease enzyme can be used. Preferably it is not from the same organism species as that being identified, since otherwise, the DNA may remain intact. (This may, in any event, identify the organism, since the enzymes are not expected to cut DNA from the species of their origin.) Since the organism species being characterized may be unknown, obtaining a suitable digest of fragments may entail a minimum amount of trial and error, which can routinely be carried out by those skilled in the art without undue experimentation. Examples of possible restriction endonuclease enzymes are Bgl I, BamH I, EcoR I, Pst I, Hind III, Bal I, Hga I, Sal I, Xba I, Sac I, Sst I, Bcl I, Xho I, Kpn I, Pvu II, Sau IIIa, or the like. See also Davis, supra, at pp. 228–230, herein incorporated by reference. A mixture of one or more endonucleases can also be used for the digestion. Normally, DNA and endonuclease are incubated together in an appropriate buffer for an appropriate period of time (ranging from 1 to 48 hours, at temperatures ranging from 25° C.–65° C., preferably 37° C.).

The resulting identifying genetic characterization will depend on the type or types of endonucleases utilized, and will be endonuclease-specific. It is therefore necessary to note which enzyme or enzymes have been used for the digestion since comparative characterizations used in a catalog should have been prepared using the same enzyme or enzymes.

An alternative step is to define endonuclease sites on the desired DNA molecules without digestion thereof, for example, by sequencing and reference to a restriction site library. Obviously, digestion is the more efficient method of noting such sites, but the method need not be limited thereto. The essence of the invention is the discovery that the position of conserved sequences along DNA, relative to the position of endonuclease restriction sites, forms a set which is characteristic for each species. Thus, any technique which yields the desired information (position of the genes visa vis position of the sites) will be useful in the invention.

Also, the position of the conserved sequences along the-DNA molecule is best noted by use of a hybridization probe. This probe is allowed to anneal to restriction fragments of the unknown's DNA. However, any other method that would allow the determination of the conserved DNA sequences, such as sequencing, would also be useful. When using the hybridization probe it is preferred to first digest and separate DNA fragments according to size, and then to hybridize the separated fragments. However, it is possible to first digest and anneal DNA with a molar excess of probe and/or sequences complementary to probe and then separate the mixture. For example, unknown DNA can be digested with a restriction endonuclease, denatured, and hybridized in liquid with a molar excess of one or more small detectably labeled DNA fragments or synthetic oligodeoxyribonucleotides complementary to a portion or portions of the conserved sequence of interest. Since most restriction enzymes cut fairly infrequently in DNA, in most cases the double-stranded region or regions of the hybrid will be small relative to the size of the restriction fragment. The hybridization reaction is conducted under conditions where only the oligodeoxyribonucleotides hybridize. The unreacted, single-stranded DNA fragments, and the DNA fragments containing the hybridized oligodeoxyribonucleotides are separated by conventional chromatographic techniques. The labeled DNA fragments will appear in predictably sized fractions. It is also possible to first anneal DNA with a molar excess of probe, then digest, and then separate the mixture. When the solution is incubated for a short time period or to a low $C_o t$, the restriction sites will be limited to the hybridized, double-stranded regions. When the solution is incubated for a long time period or to a high $C_o t$, the unknown DNA will anneal, thus creating a labeled duplex susceptible to restriction endonuclease cleavage. Unreassociated single-stranded tails may be removed with a nuclease such as S1. Unpaired bases may be filled in using DNA polymerase I or T4 polymerase.

Alternatively, one could find subsequences within the conserved sequence information (e.g. 20-, 30-, or 50- mers), which are more highly conserved than the remainder of the conserved region chosen as the probe. Those "shorter" sequences can be made synthetically or enzymatically, if desired, and may incorporate labeled nucleotides. Single-stranded, predigested DNA from the unknown is allowed to incubate with these shorter, highly conserved fragments and allowed to hybridize thereto. Separation would then be carried out on the digest mixture containing fragments partly annealed to the shorter labeled probes. (Thus, separation would occur after hybridization.) Separation could be by liquid chromatography, since the digest mixture would for all practical purposes behave as a mixture of essentially single-stranded fragments.

As indicated, a preferred method is to first digest, then separate, and then hybridize. Thus, after endonuclease digestion, the incubation mixture, which contains fragments of varying sizes, is preferably separated thereinto by an appropriate chromatographic method. Any method which is capable of separating nucleic acid digests according to size, and which allows the eventual hybridization with the nucleic acid probe when hybridization is the last step, can be used. For example, gel electrophoresis, high pressure liquid chromatography or capillary zone electrophoresis can be used. (Jorgenson, J. W., J. of HRC and CC, 4:230–231 (1981)). Presently preferred is gel electrophoresis, most preferred is agarose gel electrophoresis. In this system, the DNA digests are normally electrophoresed in an appropriate buffer, the gels are normally immersed in an ethidium bromide solution, and placed on a UV-light box to visualize standard marker fragments which may have been added. Detectably labeled standard marker fragments may be used as well.

After separation and visualization, the DNA fragments are transferred onto nitrocellulose filter paper or onto charge-modified nylon membranes by the method of Southern (Journal of Molecular Biology, 38:503–517 (1975)). The transfer can be carried out after denaturation and neutralization steps, and is usually done for long periods of time (approximately 10–20 hours) or, alternatively by means of an electrically driven transfer from gel to paper. Instruments used to accelerate the transfer from gel to paper are commercially available. The receiving nitrocellulose filter papers are then normally baked at high temperatures (60°–80° C.) for several hours, to bind the DNA to the filter.

Alternatively, transfer can be avoided by using the recent method of direct hybridization of Purrello, M. et al, Anal. Biochem., 128:393–397 (1983).

The probe utilized for the hybridization of the paper-bound DNA digest fragments is a defined nucleic acid probe preferably from or derived from a given well-defined organism or the base sequence is known.

Alternatively, the probe sequence may not have a natural conterpart; i.e., it may be a consensus sequence with a base at each position that is most commonly present at that residue in a number of equivalent sequences in different species. The consensus sequence is then generally able to form a more stable hybrid than any one of the naturally occurring sequences. The probe may be a synthetic oligodeoxyribonucleotide molecule made by covalently attaching individual nucleotides in a predetermined sequence. Synthetic molecules may be prepared, for example, by the triphosphate method of synthesis (Alvarado-Urbina et al, Science 214:270–274 (1981)). The probe molecules may be of any useful size, and more than one sequence may be in the probe solution. For example, several 20 base sequences might be used to detect several highly conserved regions in rRNA genes. It may be detectably labeled or non-labeled, preferably detectably labeled. In such case, it is either detectably labeled RNA, but preferably nick-translated labeled DNA, cloned DNA, or detectably labeled DNA which is complementary to the RNA from the probe organism (cDNA), all of which contain highly conserved DNA sequence information. Synthetic oligodeoxyribonucleotides may be prepared with detectably labeled nucleotides, so the molecule is labeled by incorporating labeled nucleotide residues. Depending on the choice of pair, the probe may be from a prokaryote, or from a eukaryote (cytoplasm-derived, or organelle derived). Most preferably, the detectable label is a radioactive label such as radioactive phosphorus (e.g., $^{32}P$, $^{3}H$ or $^{14}C$) or a biotin/avidin-based system. The nucleic acid probe may also be labeled with metal atoms. For example, uridine and cytidine nucleotides can form covalent mercury-derivatives. Mercurated nucleoside triphosphates are good substrates for many nucleic acid polymerases, including reverse transcriptase (Dale et al, *Proceedings of the National Academy of Sciences* 70:2238–2242, 1973). Direct covalent mercuration of natural nucleic acids has been described. (Dale et al, *Biochemistry* 14:2447–2457). Reannealing properties of mercurated polymers resemble those of the corresponding nonmercurated polymers (Dale and Ward, *Biochemistry* 14:2458–2469). Metal labelled probes can be detected, for example, by photo-acoustic spectroscopy, x-ray spectroscopy, e.g., x-ray fluorescence, x-ray absorbance, or photon spectroscopy.

The isolation and preparation of any desired conserved DNA sequence-containing probe is within the skill of the art. For example, the isolation of rRNA from eukaryotes or prokaryotes is well-known in the art. Thus, to prepare rRNA from eukaryotic cytoplasmic ribosomes, RNA can be extracted from whole cells or ribosomes, separated by sucrose gradient centrifugation, and the 18S and 28S fractions can be collected using known molecular weight markers. (See for example, Perry, R. P. and Kelly, D. E., "Persistent Synthesis of 5S RNA When Production of 28S and 18S Ribosomal RNA is Inhibited by Low Doses of Actinomycin D," *J. Cell. Physiol.*, 72:235–246 (1968), herein incorporated by reference). As a corollary, organelle-derived rRNA is isolated and purified from the organelle fractions in the same manner (see e.g. Van Etten, R. A. et al, *Cell*, 22:157–170 (1980), or Edwards, K. et al, *Nucleic Acids Research*, 9:2853–2869 (1981)).

If radioactively labeled probe is used, the same is isolated from the probe organism after growth or cultivation of the organism with nutrients or in culture media containing appropriately radioactive compounds. When the probe is complementary DNA (cDNA), the same is prepared by reverse transcribing isolated RNA from the probe organism, in the presence of radioactive nucleoside triphosphates (e.g., $^{32}$P-nucleosides or $^{3}$H-nucleosides).

The labeled probe may also be a nick-translated DNA molecule, especially one obtained from organelle-derived whole circular DNA. In this embodiment, chloroplast or mitochondrial DNA is nick-translated in the presence of radiolabel, and a labeled DNA probe is thereby obtained. The chloroplast labeled probe will hybridize best with chloroplast DNA, and the mitochondrial labeled probe will hybridize best with mitochondrial DNA. The chloroplast (or mitochondrial) nick-translated labeled probe will hybridize second best with mitochondrial (or chloroplast) DNA; it will also hybridize, albeit generally in less favorable fashion, with whole plant (or animal) DNA. The probe may also be obtained from eukaryotic nuclear DNA by nick-translation, although practical considerations would rule against this mode. A more useful approach in this embodiment is to cut out the highly conserved genes from the nuclear eukaryotic DNA (by restriction enzymes), separate the fragments, identify the gene sequences (as by hybridization), and isolate said gene sequences (as by electrophoresis). The isolated sequences may then be recombined into a plasmid or other vector, and after transformation of an appropriate host, cloned in $^{32}$P-containing media. Alternatively, the transformed host is grown, and the DNA is then isolated and labeled by nick-translation; or the DNA is isolated, the sequences are cut out and then labeled. The resulting ribosomal probe will hybridize in the same instances as cDNA (see infra).

The preferred nucleic acid probe is radioactively labeled DNA complementary to RNA from the probe organism. The RNA is usually messenger RNA coding for a conserved gene and is substantially free of other RNA's such as transfer RNA (tRNA) or ribosomal RNA (rRNA) (unless rRNA is used). If rRNA were to be used, prokaryotic rRNA normally contains three subspecies: the so-called 5S, 16S and 23S fragments. The reverse transcription into cDNA can be carried out with a mixture of all three, or alternatively, with a mixture of 16S and 23S fragments. It is less preferred to carry out the reverse transciption with only one of the rRNA components, although under certain conditions this may be feasible. Eukaryotic rRNA normally contains two subspecies: 18S and 28S, and the reverse transcription into cDNA can be carried out with a mixture of 18S and 28S fragments or with each.

The pure RNA, substantially free of other types of RNA, is incubated with any reverse transcriptase capable of reverse transcribing it into cDNA, preferably with reverse transcriptase from avian myeloblastosis virus (AMV) in the presence of a primer such as calf thymus DNA hydrolysate. The mixture should contain appropriate deoxynucleoside triphosphates, wherein at least one of said nucleosides is radioactively labeled, for example with $^{32}$P. For example, deoxycytidine 5'-($^{32}$P), deoxythymidine 5'-($^{32}$P), deoxyadenine 5'-($^{32}$P), or deoxyguanidine 5'-($^{32}$P) triphosphates can be used as the radioactive nucleosides. After incubation, from 30 minutes to 5 hours at 25° C.–40° C., extraction with chloroform and phenol, and centrifugation as well as chromatography, the radioactively labeled fractions are pooled, and constitute the cDNA probe. The radioactively labeled cDNA probe containing conserved DNA information in substantially purified form, i.e., free of non-labeled molecules, free of cDNA which is complementary to other types of RNA, free of proteinaceous materials as well as free of cellular components such as membranes, organelles and the like, also constitutes an aspect of the present invention. A preferred probe is prokaryotic labelled cDNA, most preferred being the bacterial labelled cDNA. The probe species can be any bacterial microorganism, such as those of the family Enterobacteriaceae, Brucella, Bacillus, Pseudomonas, Lactobacillus, Haemophilus, Mycobacterium, Vibrio, Neisseria, Bactroides and other anaerobic groups, Legionella, and the like. Although the prokaryotic examples in the present application are limited to the use of *E. coli* as a bacterial prokaryotic probe organism, this aspect of the invention is by no means limited to this microorganism. The use of cDNA in radioactively labeled form as the probe is preferred to the use of radioactively labeled RNA because DNA has greater stability during hybridization.

It is important to recognize that the labeled cDNA probe should be a faithful copy of the RNA, i.e. be one wherein all nucleotide sequences of the template RNA are transcribed each time the synthesis is carried out. The use of a primer is essential in this respect. That the cDNA is a faithful copy can be demonstrated by the fact that it should have two properties following hybridization:

1. The cDNA should protect 100% of labeled RNA from ribonuclease digestion; and

2. The labeled cDNA should specifically anneal to the RNA as shown by resistance to Sl nuclease.

Beljanski M. M. et al, C. R. Acad. Sc Paris t 286, Serie D. p. 1825–1828 (1978), described $^{3}$H radioactively labeled cDNA derived from *E. coli* rRNA. The cDNA in this work was not prepared with reverse transcriptase in the presence of a primer as in the present invention, but was prepared with a DNA polymerase I, using as a template rRNA which had been pre-cleaved using ribonuclease $U_2$. The rRNA digestion product (with RNAse $U_2$) of Beljanski et al has a different base ratio than the initial rRNA, indicating a loss of bases and/or loss of short fragments. Thus the cDNA obtained therefrom is not a faithful copy. In addition, the use of DNA polymerase I used by Beljanski is known to favor predominance of homopolymeric over heteropolymeric transcription of rRNA (see Sarin, P. S. et al, *Biochem. Biophys. Res. Comm.*, 59:202–214 (1974)).

In sum, the probe can be seen as being derived a) from genome DNA containing conserved sequences, e.g. genes, by cloning and/or nick-translation, b) from RNA itself or c) from cDNA by reverse transcription of RNA.

Normally, the next step in the process of the invention is the hybridization of the separated DNA digest from the unknown organism with the unlabeled or (preferably) radioactively labeled RNA or DNA probe. Hybridization is carried out by contacting the paper containing covalently labeled DNA digest from the unknown, with a hybridization mix containing the probe. Incubation is carried out at elevated temperatures (50°–70° C.) for long periods of time, filter papers are then washed to remove unbound radioactivity (if needed), air dried and readied for detection. An alternative, highly preferred hybridization, which is much more rapid than the one described above, is the room temperature phenol emulsion reassociation technique of Kohne, D. E. et al, *Biochemistry*, 16:5329–5341 (1977), which is herein incorporated by reference.

After hybridization, the technique requires selective detection of the appropriately hybridized fragments. This detection can be carried out by taking advantage of the double strandedness of the hybridized fragments and using a selective method therefor (for non-labeled probe), or by autoradiography or by an appropriate radiation scanner which may or may not be computerized, and which may increase the speed of detection (for labeled probe). These techniques are well known to those skilled in the art and will not be further described at this point.

The end product of the technique is an identifying genetic characterization, such as a chromatographic band pattern having peaks and troughs, or preferably, light and dark regions of various intensities, at specific locations. These locations can be readily matched to specific fragments sizes (in kilobase pairs) by introduction into the separation technique of a marker, such as EcoR I digested λ bacteriophage DNA. In this manner, both the relative position of the bands to each other, as well as the absolute size of each band can be readily ascertained. The identifying genetic characterization for the unknown is then compared with characterizations present in a catalog or library. The catalog or library can consist of a book containing characterizations for at least two, and up to a virtually unlimited number of defined different organisms genera and species. For example, the number of pathologically relevant bacteria that cause human disease is estimated to be about 100, so it is estimated that a standard catalog of pathogenic bacteria would contain anywhere between 50 and 150 such characterizations. A catalog of types of bacterial strains for epidemiological typing systems can also be included.

The characterizations will depend on the type or types of endonuclease enzymes selected, possibly on the particular organism used as the source for the radioactively labeled probe (the probe organism), and on the composition of the conserved DNA sequence information nucleic acids utilized to prepare the probe (e.g. containing either prokaryotic rRNA 5S, 16S or 23S subtypes, or only 16S and 23S, or consensus sequences or the like). Thus, the catalog may, for each probe, contain a variety of enzyme-specific characterizations, with the size of each band listed, and with the relative intensity noted. As the concentration of the bound DNA bound to the filter decreases, only the most intense bands can be seen, and the size of this band or bands can thus identify species. Any variation or permutation of the above can of course be used for the library. Additionally, for a eukaryotic organism the library may contain patterns that result from the use of one type of DNA or any combination of organelle and/or nuclear DNA. The pattern for each DNA digest will depend on the probe composition. The catalog may be arranged so that if more than one strain or species is present in the extracted sample and detected by the probe, the resulting characterization can be interpreted.

A user can either compare the obtained characterization, e.g., band pattern, visually, or by aid of a one-dimensional, computer assisted, digital scanner programmed for recognition of patterns. These computer scanners are well known in the art of the time-of-sale transactions (the commonly utilized "supermarket" check-out pattern readers). Ideally, the library or catalog is present in a computer memory both in terms of the relative characterizations for a plurality of organisms, and in terms of the absolute values of molecular weight or size of the fragments. The catalog comparison then consists of matching the unknown characterization with one of the characterizations present in the library by means of either one or both of the stored information elements (relative characterizations and/or absolute size elements). The intensity of each band when compared to a standard can also reveal the amount of bound DNA hybridized, and thus can be used to estimate the extent of the presence of an organism, for example a prokaryote in a eukaryote.

If a user wishes to further confirm the nature and identification of a given organism, such user can digest the unknown with a second, different endonuclease, and compare the resulting characterization to catalog characterizations of the organism for the second chosen endonuclease. This process can be repeated as many times as necessary to get an accurate identification. Normally, however, a single analysis with a single probe would be sufficient in most instances.

The present invention and its variations can be used for a myriad of applications. It may be used by plant or animal breeders to correctly identify their subjects, or it may be used by clinical and microbiological laboratories to identify bacteria, parasites or fungi present in any medium, including in eukaryotic cells. In this latter use, the method is preferred to the standard microbiological assays, since it does not require microbiological assays, since it does not require isolation and growth of the microbes. In vitro growth and characterization is now either impossible for some microorganisms such as *Mycobacterium leprae* (agent of leprosy), impossible on standard media for some microorganisms such as the obligate intracellular bacteria (e.g. rickettsia, chlamydia, etc), or highly dangerous (e.g. *B anthracis* (agent of anthrax)). The present method depends on the isolation of nucleic acid and avoids these problems since it avoids conventional bacterial isolation and characterization. The method is expected to detect microorganisms that have not yet been conventionally described. In addition, the present method allows distinguishing different strains of species, and this can be useful, for example, for epidemiological typing in bacteriology. The method can be used by forensic laboratories to correctly and unambiguously identify plant or animal tissues in criminal investigations. It can also be used by entomologists to quickly identify insect species, when ascertaining the nature of crop infestations.

In addition, upon the conjunction of the method with the identification of infrasubspecific taxons (such as e.g., nitrogenase genes in plant roots, see Hennecke, H. 291 *Nature* 354 (1981)), the methodology can be utilized to search for and identify the genotypes of individual strains.

The method of this invention is preferably used for the identification of microorganisms wherever they may be found. These microorganisms may be found in physiological as well as non-physiological materials. They may be found in industrial growth media, culture broths, or the like, and may be concentrated for example by centrifugation. Preferably, the microorganisms are found in physiological media, most preferably they are found in animal sources infected therewith. In this latter embodiment, the method is used to diagnose bacterial infections in animals, most preferably in humans. The detection and identification of bacterial DNA with a prokaryotic probe is highly selective and occurs without hindrance, even in the presence of animal, (e.g., mammalian) DNA. If a prokaryotic probe is used, conditions can be selected which minimize hybridization with mitochondrial DNA, or mitochondrial bands can be subtracted from the pattern. The technique can thus be used in clinical laboratories, bacterial depositories, industrial fermentation laboratories, and the like.

Of particular interest is the possibility of detecting, in addition to the species and strain identity of the infecting microorganism, the presence in the microorganism of any specific genetic sequences. For example, it is possible to detect the presence of antibiotic resistance sequences found on R factors, which are transmissible plasmids mediating drug resistance. One can add labeled R-factor DNA or cloned labeled antibiotic resistance sequences to the hybridization mixture in order to correctly determine the antibiotic resistance of the organism, (an extra band or bands would appear), or one can rehybridize the once hybridized filter in the presence of added antibiotic resistance sequence probe or probes. Alternatively one could separate the unknown DNA into aliquots, and test the first aliquot for identification, the second for the presence of drug resistance sequences, the third for toxin genes, etc. Alternatively, one could use conserved gene information containing probe labeled with one radionuclide (e.g. $^{32}P$) in a hybridization mixture with added R-factor probe labeled with a different radionuclide (e.g. $^{3}H$ or $^{14}C$). After hybridization, the presence of R-factor DNA in the unknown DNA can be tested by scanning with two different scanners: one for species and strain identification (e.g. $^{32}P$), the other for drug resistance, or the like (e.g. $^{3}H$ or $^{14}C$). In this manner the lab can, without isolating and characterizing the microorganism, identify the genus and species, type the strain and test for drug resistance, possible toxin production or any other character or taxon below the rank of species that can be detected with a labeled nucleic acid sequence or probe, all in one experiment.

The R-factors are universal and cross species boundaries, so that identification can be carried out in any bacterial genus or species with the same R-factor probe (see Tomkins, L. S. et al, *J. Inf. Dis.*, 141:625–636 (1981)).

In addition, the presence of viruses or virus-related sequences in eukaryotes or prokaryotes can also be detected and identified in conjunction with the method of the invention: Any of the viruses described in "*Manual of Clinical Microbiology*", 3d edition, edited by Lennette, E. H., *Amer. Soc. Microb.*, 1980, 774–778 can be identified, e.g., picornaviridae, caliciviridae, reoviridae, togaviridae, orthomyxoviridae, paramyxoviridae, rhabdoviridae, retroviridae, arenaviridae, coronaviridae, bunyaviridae, parvoviridae, papovaviridae, adenoviridae, herpesviridae, vidoviridae and poxviridae.

A) When the viral genome is integrated into host DNA (as with DNA viruses, for example members of Papovaviridae, and RNA viruses, for example, members of Retroviridae), high molecular weight DNA is extracted from the tissue and digested with restriction endonucleases. The overall procedure is the same as used for bacteria. The choice of a viral probe again depends on the question asked, and on the extent of homology between the "probe virus" and the viral related sequences to be detected. In order to have suitable sequence homology, it may be necessary that the probe and tissue sequences are related to the same family, genus, or species of virus. In addition to the extent of conserved sequences, whether or not a viral probe hybridizes to viral related sequences in host DNA may be determined by the hybridization conditions, which can be stringent or relaxed. The result of the hybridization will be a band or a pattern of bands showing that there are viral sequences incorporated into the host DNA. This information may be useful in helping to predict the occurrence of cancer. The probe can be any labelled complementary nucleic acid probe including cloned viral sequences. For RNA viruses, for example viral RNA can be used to make a DNA with reverse transcriptase; for DNA viruses, for example, viral DNA labelled by nick translation can be used. Again multiple probes can be used, especially with different labels.

Same general features apply equally to DNA and RNA viruses. Viral genomes are relatively small, so the precipitated nucleic acid is preferably collected by centrifugation; all of the procedures can use the total nucleic acid or the various procedures can be run separately. It is expected that viral nucleic acid can be concentrated by spooling cellular DNA to remove it before centrifugation. This can also be used to determine if the viral genome is integrated.

For the viral probe to hybridize, it may be necessary and at least most preferred that the probe be from the same family, genus, or species as the unknown. Reaction conditions, stringent or relaxed, may determine whether or not a given probe hybridizes a distantly related genome. The probe may be cloned viral sequences that are labeled, or may be the complete genome or a portion of it.

The technique described by Southern, supra is useful for the transfer of large DNA fragments (greater than about 0.5 kilobases) to nitrocellulose paper after alkali denaturation. This technique might be useful for DNA viruses but not for RNA viruses. RNA has been transferred and covalently coupled to activated cellulose paper (diazobenzyloxymethyl-paper), and this can be used for RNA viruses. The modification of the Southern technique by Thomas (Thomas, P., *Proc. Nat. Acad. Sci.*, USA, 77:5201–5205 (1980)) can be used for the efficient transfer of RNA, and small DNA fragments to nitrocellulose paper for hybridization. RNA and small DNA fragments are denatured with glyoxal and dimethyl sulfoxide, and electrophoresed in agarose gel. This procedure transfers DNA fragments between 100 and 2000 nucleotides and RNA efficiently, and they are retained on the nitrocellulose paper during hybridization. This is useful for small ribosomal DNA fragments as well. So it is most preferred to divide the restriction-enzyme digested specimen and denature the nucleic acid in one portion with glyoxal. The Southern and Thomas procedures would yield a maximum amount of information.

B) For DNA viruses, restriction analysis can be carried out with double-stranded (DS) viral DNA's to identify viruses present. Single-stranded (SS) DNA viruses will have different genome lengths. The probe (the sequence information could be converted to DS DNA) that hybridizes, the hybridized fragment pattern and/or the sizes or size can be used to identify viruses. There are again a number of ways to obtain complementary nucleic acid probes. For example, for DS DNA nick-translation can be used; for SS DNA, DNA polymerase can be used to synthesize a cDNA.

C) For RNA viruses, RNA is not digested by restriction endonucleases (the sequence information could be converted to DS DNA). The genomes of different RNA viruses are of different sizes, and some RNA viruses have more than 1 molecule in their genome. This, along with the base sequences detected by certain probes or pooled probes allows the RNA viruses to be identified. An example of a probe would be cDNA synthesized using viral RNA.

When searching for infectious agents in specimens it is possible to search directly by extracting nucleic acid from the specimen, or by culturing first in media or cells to increase the number of agents, or by using a concentration step such as centrifugation, or by trying all approaches.

The present invention lends itself readily to the preparation of "kits" containing the elements necessary to carry out the process. Such a kit may comprise a carrier being compartmentalized to receive in close confinement therein one or more container means, such as tubes or vials. One of said container means may contain unlabeled or detectably labeled nucleic acid probe, such as for example the radioactively labeled cDNA to RNA from the organism probe, (preferably prokaryotic cDNA in the case of a kit to identify bacteria). The labeled nucleic acid probe may be present in lyophilized form, or in an appropriate buffer as necessary. One or more container means may contain one or more endonuclease enzymes to be utilized in digesting the DNA from the unknown organism. These enzymes may be present by themselves or in admixtures, in lyophilized form or in appropriate buffers. Ideally, the enzymes utilized in the kit are those for which corresponding catalogs have been prepared. Nothing stops the user, however, from preparing his or her own comparative standard at the moment of experiment. Thus, if a user suspects that an unknown is in fact of a given genus or species, he or she may prepare the identifying characteristics for the known and compare it with the characterization for the unknown. The kit may thus also contain all of the elements necessary in order to carry out this sub-process. These elements may include one or more known organisms, (such as bacteria), or isolated DNA from known organisms. In addition, the kit may also contain a "catalog", defined broadly as a booklet, or book, or pamphlet, or computer tape or disk, or computer access number, or the like, having the identifying characterizations for a variety of organisms of a certain group, such as plant species, mammal species, microbe species, especially pathologically important bacteria, insect species or the like. In this mode, a user would only need to prepare the characterization for the unknown organism, and then visually (or by computer) compare the obtained characterization with the characterizations in the catalog. The kit may also contain in one container probe RNA for probe synthesis, in another container radiolabeled deoxyribonucleoside triphosphate, and in another container primer. In this manner the user can prepare his or her own probe cDNA.

Finally, the kit may contain all of the additional elements necessary to carry out the technique of the invention, such as buffers, growth media, enzymes, pipettes, plates, nucleic acids, nucleoside triphosphates, filter paper, gel materials, transfer materials, autoradiography supplies, and the like. It may also contain antibiotic resistance sequence probes, viral probes, or other specific character probes.

Having now generally described this invention, the same will be better understood by reference to certain specific examples which are included herein for purposes of illustration only and are not intended to be limiting of the invention, unless specified.

MATERIALS AND METHODS

A. Bacterial
Extraction of High Molecular Weight DNA

Bacterial broth cultures were centrifuged and the cells were washed with cold saline. The cells were suspended in a volume measured in ml of extraction buffer (0.15 M sodium chloride, 0.1 M EDTA, 0.03 M tris pH 8.5) approximately 10 times the gram weight of the packed cells. Lysozyme at 10 mg/ml was added to 0.5 mg/ml final concentration. The suspension was incubated at 37° C. for 30 minutes. Cell disruption was completed by the addition of 25% SDS to 2.5% final concentration, and raising the temperature to 60° C. for 10 minutes. After cooling in a tap water bath, mercaptoethanol was added to 1% final concentration. Pronase® at 20 mg/ml in 0.02 M tris pH 7.4 was predigested at 37° C. for 2 hours and then added to 1 mg/ml final concentration. The solution was incubated at 37° C. for 18 hours. Phenol was prepared by mixing one liter redistilled phenol, 2.5 liters double distilled water, 270 ml saturated Tris base, 12 ml mercaptoethanol, and EDTA to $10^{-3}$M final concentration and allowing the mixture to separate at 4° C. The phenol was washed with wash buffer ($10^{-1}$M sodium chloride, $10^{-3}$M EDTA, 10 mM tris pH 8.5). Then an equal volume of fresh buffer was added. Mercaptoethanol was added to 0.1% final concentration. The solution was mixed and stored at 4° C. One half volume prepared phenol and one half volume chloroform was added to the lysed cell solution. This was shaken for approximately 10 minutes and centrifuged at 3,400×g for 15 minutes. The aqueous phase was removed with an inverted 25 ml glass pipette. The extraction procedure was repeated until there was little precipitate at the interface. One-ninth volume 2 N sodium acetate pH 5.5 was added to the aqueous phase. Two times volume of 95% ethyl alcohol at −20° C. was poured slowly down the side of the flask. The end of a Pasteur pipette was melted close and used to spool the precipitated DNA. High molecular weight DNA was dissolved in buffer ($10^{-3}$EDTA, $10^{-2}$M tris pH 7.4). The concentration of DNA was determined by absorbance at 260 nm using 30 micrograms per absorbance unit as conversion factor.

Restriction Endonuclease Digestion of DNA.

EcoR I restriction endonuclease reactions were performed in 0.1 M tris-HCl pH 7.5, 0.05 M NaCl, 0.005 M MgCl₂, and 100 micrograms per ml bovine serum albumin. EcoR I reaction mixtures contained 5 units of enzyme per microgram of DNA, and were incubated four hours at 37° C. PST I restriction endonuclease reactions were performed in 0.006 M tris-HCl pH 7.4, 0.05 M sodium chloride, 0.006 M magnesium chloride, 0.006 M 2-mercaptoethanol, and 100 micrograms per ml of bovine serum albumin. PST I reaction mixtures contained 2 units of enzyme per microgram DNA, and were incubated four hours at 37° C. Usually 10 micrograms DNA was digested in a final volume of 40 microliters. Ten times concentration buffers were added. Sterile distilled water was added depending on the volume of DNA. λ Bacteriophage DNA was restricted with EcoR I to provide marker bands for fragment size determinations. Usually 2 micrograms λ DNA was digested with 20 units EcoR I in a final volume of 20 microliters.

Gel Electrophoresis and DNA Transfer.

DNA digests were supplemented with glycerol, to about 20%, and bromophenol blue tracking dye. In the case of λ DNA digests, 20 microliters of 1x EcoR I buffer was added to each 20 microliter reaction mixture. Usually 15 microliters 75% glycerol and 5 microliters 0.5% bromophenol blue were added to each 40 microliter reaction mixture.

10 micrograms digested bacterial DNA or 2 micrograms digested λ DNA were loaded per well and overlaid with molten agarose. Digests were electrophoresed in 0.8% agarose with 0.02 M sodium acetate, 0.002 M EDTA, 0.018 M tris base, and 0.028 M tris HCl pH 8.05 at 35 V until the dye migrated 13 to 16 cm. Gels were then immersed in ethidium bromide (0.005 mg/ml) and placed on a UV-light box to visualize the λ fragments. DNA was transferred to nitrocellulose filter paper by the method of Southern, supra. Gels were treated with denaturing solution (1.5 M sodium chloride, 0.5 M sodium hydroxide) on a rocker table for 20 min. Denaturing solution was replaced with neutralization solution (3.0 M sodium chloride, 0.5 M tris HCl, pH 7.5), and after 40 minutes the gels were checked with pH paper. Following neutralization, the gels were treated with 6×SSC buffer (SSC=0.15 M sodium chloride, 0.015 M sodium citrate) for 10 minutes. DNA fragments were transferred from the gel to the nitrocellulose paper by drawing 6 X SSC through the gel and nitrocellulose paper with a stack of paper towels for 15 hours. Filters were placed between two sheets of 3 MM chromatography paper, wrapped in aluminum foil, shiny side out, and dried in a vacuum oven at 80° C. for 4 hours. Synthesis of $^{32}$P ribosomal RNA Complementary DNA ($^{32}$P rRNA cDNA).

$^{32}$P-labeled DNA complementary to *E. coli* R-13 23S and 16S ribosomal RNA was synthesized using reverse transcriptase from avian myeloblastosis virus (AMV). The reaction mixture contained 5 microliters 0.2 M dithiothreithol, 25 microliters 1 M tris pH 8.0, 8.3 microliters 3 M potassium chloride, 40 microliters 0.1 M magnesium chloride, 70 micrograms actinomycin, 14 microliters 0.04 M dATP, 14 microliters 0.04 M dGDP, 14 microliters 0.04 M dTTP and 96.7 microliters H$_2$O. The following were added to a plastic tube: 137.5 microliters reaction mixture, 15 microliters calf thymus primer (10 mg/ml), 7 microliters H 20, 3 microliters rRNA (using 40 micrograms/OD unit concentration, is 2.76 micrograms/microliters ), 40 microliters deoxycitydine 5'-($^{32}$P) triphosphate (10 mCi/ml), and 13 microliters AMV polymerase (6,900 units µl. The enzymatic reaction was incubated 1.5 hours at 37° C. Then the solution was extracted in 5 ml each of chloroform and prepared phenol. After centrifugation (JS 13,600 RPM), the aqueous phase was layered directly on a Sephadex® G-50 column (1.5×22 cm). A plastic 10 ml pipette was used for the column. A small glass bead was placed in the tip, rubber tubing with a pinch clamp was attached, and degassed G-50 swelled in 0.05% SDS overnight was added. The aqueous phase wall allowed to flow directly into the G-50 and was then eluted with 0.05% SDS. 20 fractions at 0.5 ml each were collected in plastic vials. Tubes containing peak fractions were detected by Cerenkov counting using a $^3$H discriminator, counting for 0.1 min. per sample and recording total counts. Peak fractions were pooled. Aliquots were added to Aquesol® (commercially available), and the CPM of $^{32}$P per ml was determined by scintillation counting.

Hybridization and Autoradiography.

Fragments containing ribosomal RNA gene sequences were detected by autoradiography after hybridization of the DNA on the filters to $^{32}$P-rRNA cDNA. Filters were soaked in hybridization mix (3×SSC, 0.1% SDS, 100 micrograms/ml denatured and sonicated canine DNA, and Deinhart's solution (0.2% each of bovine serum albumen, Ficoll, and polyvinyl pyrrolidine)), for 1 hour at 68° C. $^{32}$P rRNA cDNA was added at 4×10$^6$ CPM/ml, and the hybridization reaction was incubated at 68° C. for 48 hours. Filters were then washed in 3×SSC, and 0.1% SDS at 15 min. intervals for 2 hours or until the wash solution contained about 3,000 cpm $^{32}$P per ml. Filters were air dried, wrapped in plastic wrap and autoradiographed approximately 1 hour with Kodak X-OMAT R film at −70° C.

B. Mammalian experiments. *Mus musculus domesticus* (mouse) rRNA probes were synthesized from 18S and 28S, and only 28S rRNA. Nucleic acid was extracted from mouse liver and precipitated. High molecular weight DNA was spooled and removed. The remaining nucleic acid was collected by centrifugation and dissolved in buffer, 50 mM MgCl$_2$ and 100 mM Tris pH 7.4. DNAse (RNAse free) was added to a concentration of 50 µg/ml. The mixture was incubated at 37° C. for 30 min. The resulting RNA was rextracted, ethanol precipitated, and dissolved in 1 mM sodium phosphate buffer pH 6.8 A 5 to 20% sucrose gradient in 0.1M Tris pH 7.4 and 0.01M EDTA was prepared. The sample was added and the gradients spun in an SW40 rotor 7 hr. at 35K RPM. Fractions were collected by optical density. The 18S and 28S fractions were selected by comparison to known molecular weight markers.

For all of the mammalian experiments relaxed hybridization conditions were used, 54° C. The washing procedure, carried out at 54° C., was 3 separate washes with 3×SSC with 0.05% SDS for 15 min. each.

Examples 1–8 describe experiments carried out with rRNA-information containing probes. Examples 9–11 describe computer simulations utilizing a histone gene information-containing probe, a tryptophan operon trp D gene-information containing probe, and an α-fetoprotein gene information-containing probe, respectively.

EXAMPLE 1

Bacterial Species are Defined by Restriction Endonuclease Analysis of Ribosomal RNA Genes The several strains of *P. aeruginosa* used in this example have the minimal phenotypic characters which identify the species (Hugh R. H., et al, in: Manual of Clinical Microbiology, 2d Ea. ASM, 1974, pp. 250–269). (Table 2). Strains of three other Pseudomonas and two Acinetobacter species were selected to compare species and genera (Table 3).

TABLE 2

| Corresponding strain numbers of isolates with the minimal phenotypic characters of *P. aeruginosa* for the comparison of Strains. | |
|---|---|
| RH | ATCC |
| 151 | 10752 |
| 809 | 7701 |
| 810 | 8689 |
| 811 | 8707 |
| 812 | 8709 |
| 815 | 10145 |
| 1559 | 14425 |

Strains used for comparison of Pseudomonas and Acinetobacter species are listed in Table 3.

TABLE 3

Corresponding strain numbers of type, neotype and reference strains for the comparison of species and genera

| Species | RH | ATCC | NCTC | Strain Status |
|---|---|---|---|---|
| P. aeruginosa | 815 | 10145 | 10332 | type |
| P. stutzeri | 2601 | 17588 | | neotype |
| P. fluorescens | 818 | 13525 | 10038 | neotype |
| P. putida | 827 | 12633 | | neotype |
| A. anitratus | 2208 | 19606 | | type |
| A. lwoffii | 462 | 7976 | | reference |

Acinetobacter species were selected for comparison of genera because they share certain attributes with many Pseudomonas species.

The sizes (kilobase pairs) of fragments in EcoR I digests are: P. stutzeri 16.0, 12.0, 9.4; P. fluorescens 16.0, 10.0, 8.6, 7.8, 7.0; P. putida 24.0, 15.0, 10.0, 8.9; A. anitratus 20.0, 15.0, 12.5, 9.8, 7.8, 6.1, 5.2, 4.8, 3.8, 2.8 (size of the smallest 3 fragments not calculated); A. lwoffii 12.0, 10.0, 9.1, 7.0, 6.4, 5.7, 5.5, 5.3, 4.8, 4.4, 3.6, 3.2, 2.9 (size of the smallest 3 fragments not calculated). The sizes (kilobase pairs) of fragments in PST I digests are; P. stutzeri 6.7, 6.1, 5.5; P. fluorescens 10.0, 9.4, 7.8, 7.0; P. putida 10.5, 9.9, 6.8, 6.3, 4.4; A. anitratus 36.0, 28.0, 20.5, 12.0, 10.0, 5.8, 3.7, 2.6, 2.4; A. lwoffi 9.9, 8.7, 7.2, 5.7, 4.0, 3.6, 3.2, 2.7.

Figure 2:
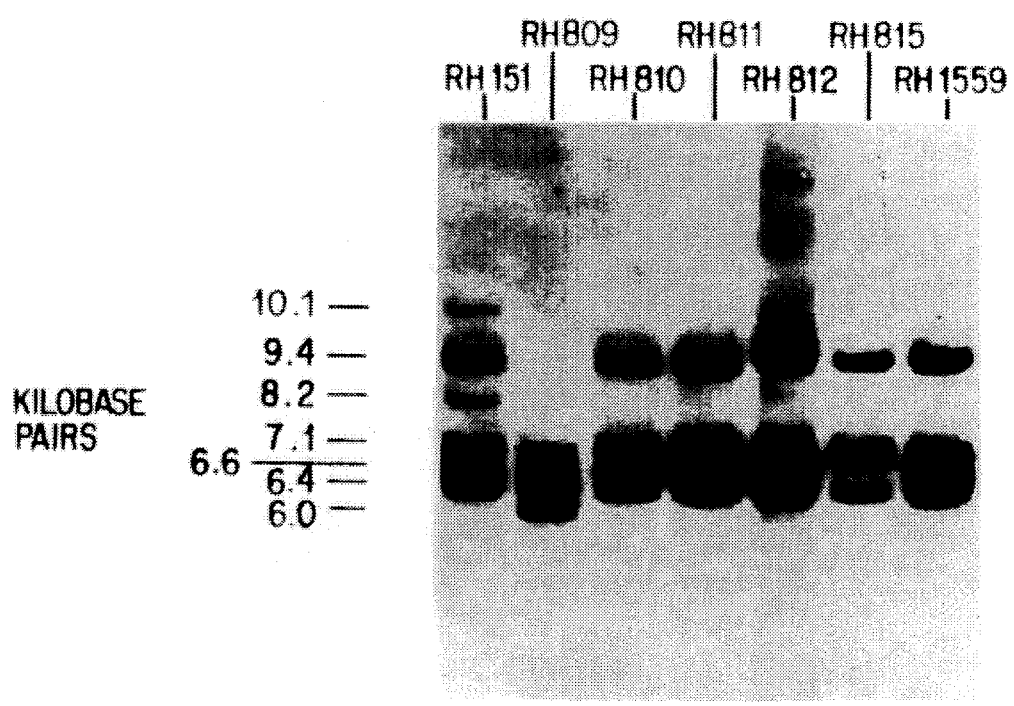
FIG. 2 shows the Pst I restriction endonuclease digest of DNA isolated from strains of *P. aeruginosa*, using cDNA to 16S and 23S rRNA of *E. coli* as the probe.

Comparison of the hybridized restriction fragments from the seven strains of P. aeruginosa leads to the conclusion that this species can be defined by an EcoR I specific set of fragments containing rRNA gene sequences, 10.1, 9.4, 7.6, and 5.9 kilobase pairs (KBP) (FIG. 1). The 7.6 KBP EcoR I fragment occurs in 4 of the 7 strains in this sample. An analogous situation occurs among certain phenotypic characters of strains of species. The fact that the EcoR I sets of fragments from the 7 strains can be used to separate the strains into two groups prompts speculation that there may be two species with the minimal phenotypic characters of P. aeruginosa. The results of experiments in which DNA was digested with PST I (FIG. 2) lead to the conclusion that the strain variation shown by the EcoR I 7.6 KBP fragment represents variation within the species, since there is a single conserved set of PST I fragments, 9.4, 7.1, 6.6, and 6.4 KBP, that define the species. The 9.4 and 6.6 KBP Pst I fragments occur in 6 of the 7 strains of P. aeruginosa; the 7.1 and 6.4 KBP PST I fragments occur in all of the strains sampled. PST I fragment variation occurs in strains that do not contain an EcoR I 7.6 KBP fragment; RH 151 has 10.1 and 8.2 KBP fragments, RH 809 does not contain a 9.4 KBP fragment and has a 6.0 KBP fragment, and RH 815; the type strain, does not contain a 6.6 KBP fragment. The patterns of hybridized fragments support the conclusion that enzyme specific, conserved sets can be used to define species. Strains of a species probably have a majority of the fragments in the conserved set. The occurrence of fragment variations in some strains does not prevent identification and may prove useful in epidemiological studies.

Figure 3:
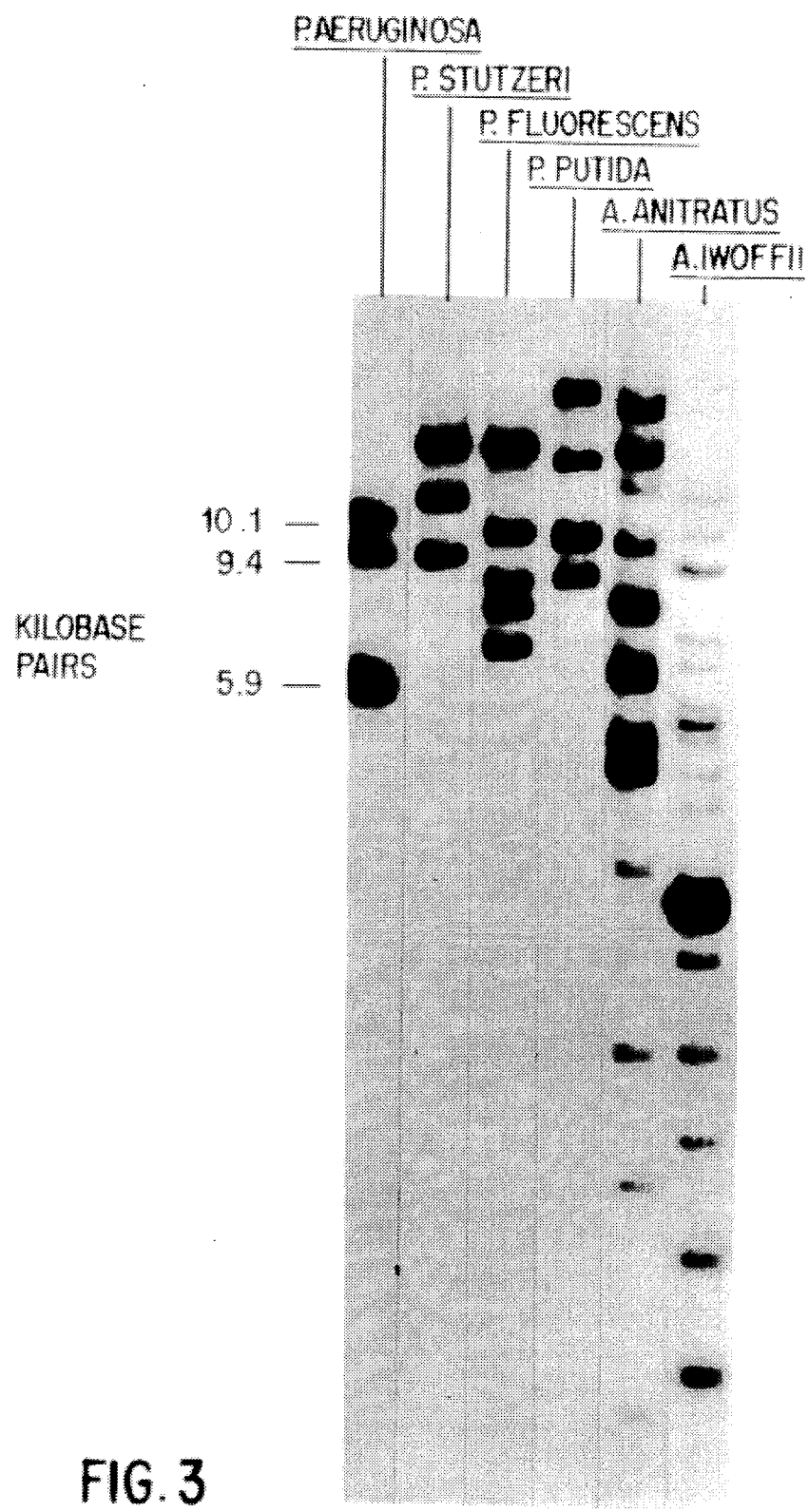
FIG. 3 shows the EcoR I restriction endonuclease digest of DNA isolated from species of glucose-nonfermenting, gram-negative rods, using cDNA to 16S and 23S rRNA of *E. coli* as the probe.
Figure 4:
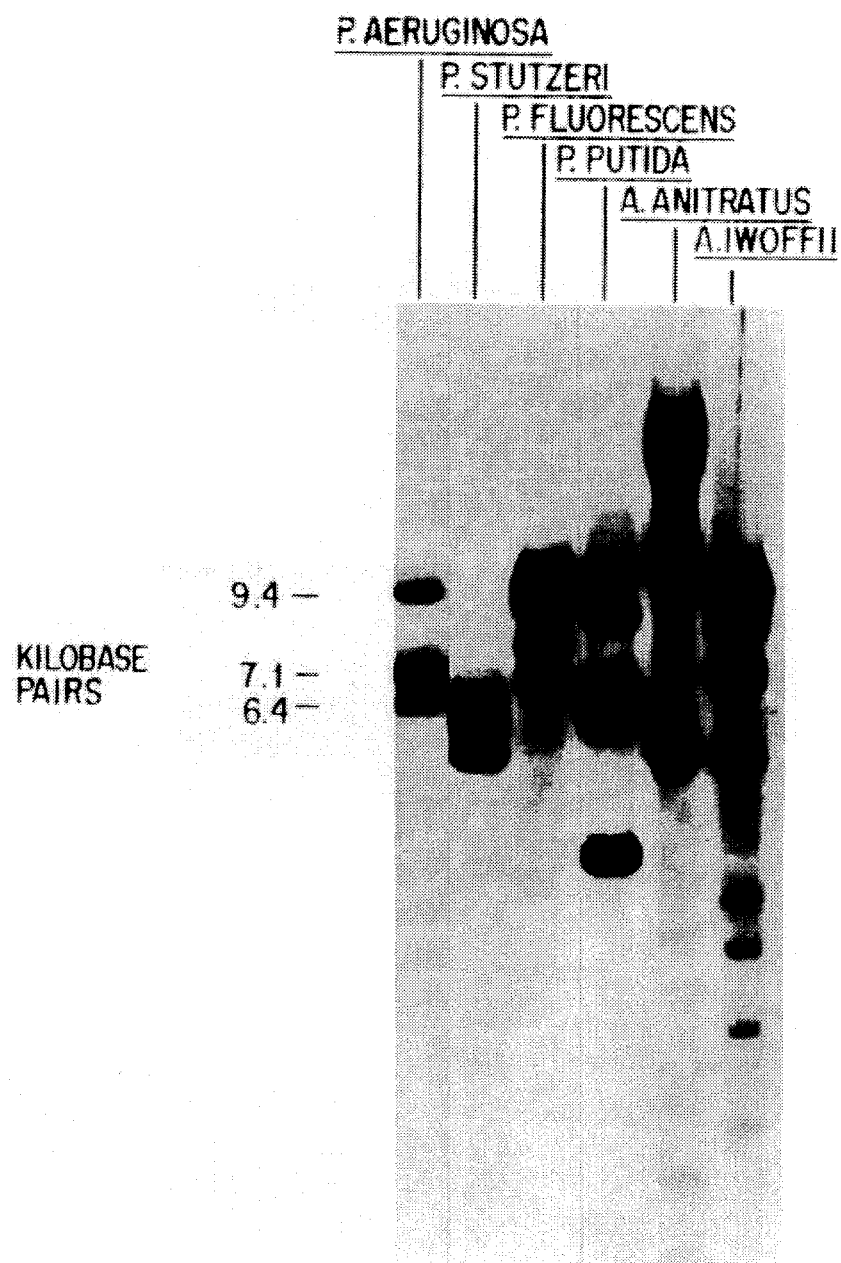
FIG. 4 shows the Pst I restriction endonuclease digest of DNA isolated from species of glucose-nonfermenting, gram-negative rods using cDNA to 16S and 23S rRNA of *E. coli* as the probe.

The occurrence of variation, EcoR I 7.6 KBP fragment in P. aeruginosa strains, may be put into perspective by examining hybridized EcoR I fragments found in the type strains of other Pseudomonas species (FIG. 3). The type strains of P. stutzeri, P. fluorescens, and P. putida do not contain a 7.6 KBP fragment, but do have EcoR I fragments of the sane size in common; P. aeruginosa and P. stutzeri each have a 9.4 KBP fragment, P. stutzeri and P. fluorescens each have a 16 KBP fragment, and P. fluorescens and P. putida each have a 10 KBP fragment. In general, the sizes of the fragments are unique in the type strains of each of the 4 Pseudomonas species; and the type strain of each species has a different size range of fragments. These general comments are also true for the PST I digests (FIG. 4).

When the fragment patterns or one strain of each of the 4 Pseudomonas and 2 Acinetobacter species are compared, it can be concluded that the species of each genus are similar, but the genera differ. The 2 Acinetobacter species have a greater range of hybridized fragment sizes than do the 4 Pseudomonas species.

Without the aid of restriction enzyme maps such as those availble for E. coli. Bacillus thuringiensis and B. subtilis, it is not possible to predict where enzymes cut rRNA genes, the number of copies per genome, whether there are heterologous flanking regions between genes or gene heterogeneity. The E. coli rRNA cDNA probe may fail to hybridize with some restriction fragments containing rRNA gene sequences, and if so, this reflects the evolutionary distance or diversity between the test organism and E. coli. The conserved nature of rRNA can be used to argue that this is not the case. However, this is a minor problem compared to the advantage of having a standard probe that can be equally applied to any unknown species.

EXAMPLE 2

Comparison of Restriction Analysis with DNA—DNA Liquid Hybridization:

The strains used in this study are listed in Tables 4 and 5.

TABLE 4

Corresponding Strain Numbers of Neotype strains of B. subtilis and type strains of junior synonyms

| Species | RH | ATCC | Strain Status |
|---|---|---|---|
| B. subtilis | 3021 | 6051 | neotype |
| B. uniflagellatus | 2990 | 15134 | type |
| B. amyloliquafaciens | 3061 | 23350 | type |

TABLE 5

Corresponding strain number of strains of B. subtilis

| RH | NRRL | ATCC |
|---|---|---|
| 3063 | B-354(NRS-231) | 6633 |
| 3064 | B-356(NRS-238) | 7067 |
| 3065 | NRS-265 | 6455 |
| 3066 | NRS-659 | 7060 |
| 3067 | NRS-730 | 7003 |
| 3068 | NRS-737 | 943 |
| 3069 | NRS-741 | 4344 |
| 3070 | NRS-773 | 8188 |
| 3071 | NRS-1106 | 4944 |
| 3072 | NRS-1107 | 7480 |

High molecular weight DNA was isolated from each of the strains. Liquid DNA—DNA hybridization data was collected using RH 3021 and RH 2990 labeled DNAs and results are shown in Table 6.

TABLE 6

Percent hybridization between labeled DNA probe and DNA from strains of *B. subtilis*

| Labeled DNA probe | RH 3063 | RH 3064 | RH 3066 | RH 3067 | RH 3068 | RH 3065 |
|---|---|---|---|---|---|---|
| RH 3021 | 61 | 77 | 51 | 96 | 84 | 18 |
| RH 2990 | 12 | 10 | 13 | 15 | 16 | 50 |
|  | RH 3069 | RH 3070 | RH 3071 | RH 3072 | RH 3021 | RH 2990 |
| RH 3021 | 14 | — | 93 | 15 | 100 | 20 |
| RH 2990 | 100 | — | 17 | 100 | 20 | 100 |
|  | RH 3061 |  |  |  |  |  |
| RH 3021 | 11 |  |  |  |  |  |
| RH 2990 | 70 |  |  |  |  |  |

Figure 5:
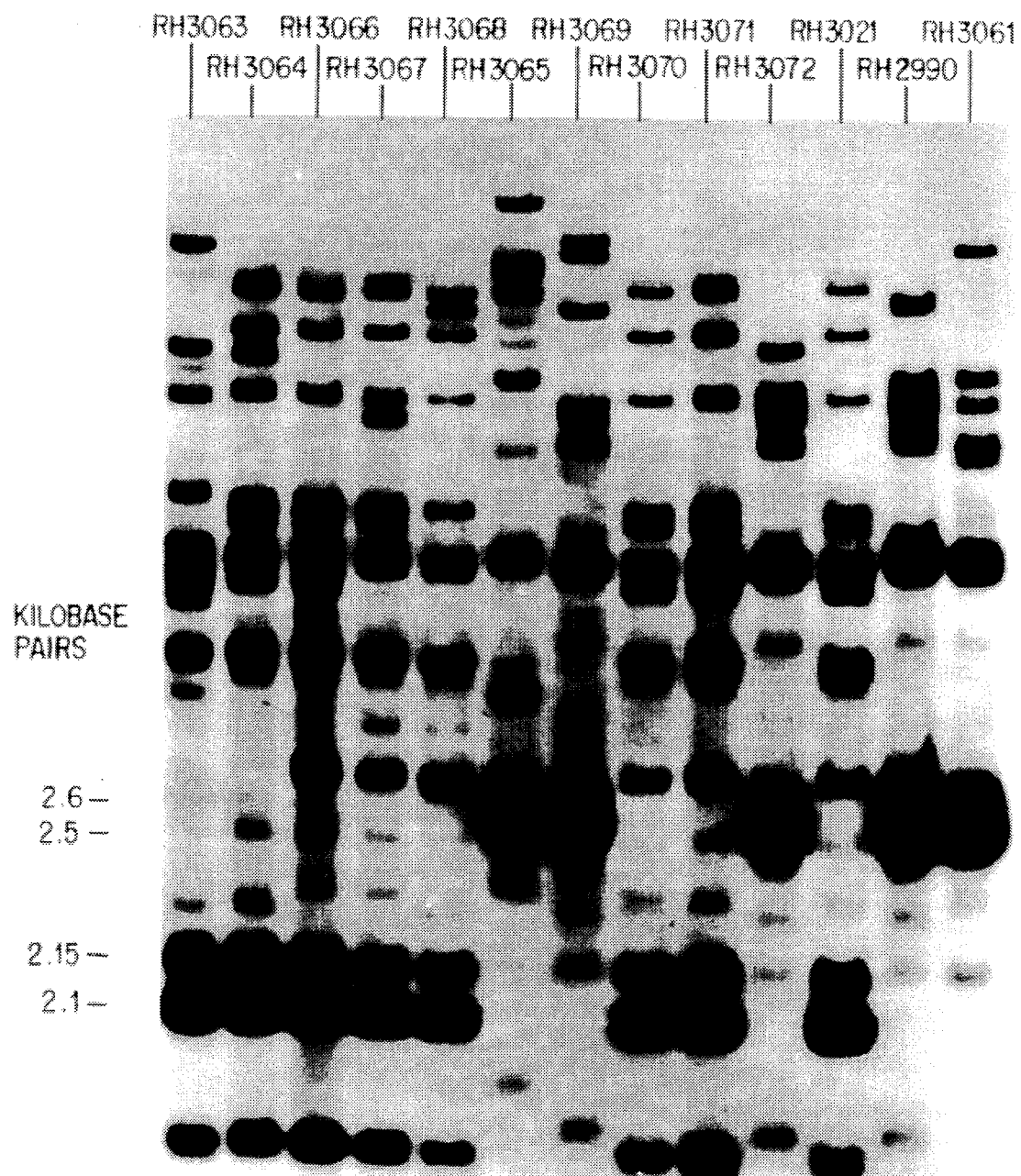
FIG. 5 shows the EcoR I restriction endonuclease digest of DNA isolated from various *Bacillus subtilis* strains, using cDNA to 16S and 23S rRNA of *E. coli* as the probe.
Figure 6:
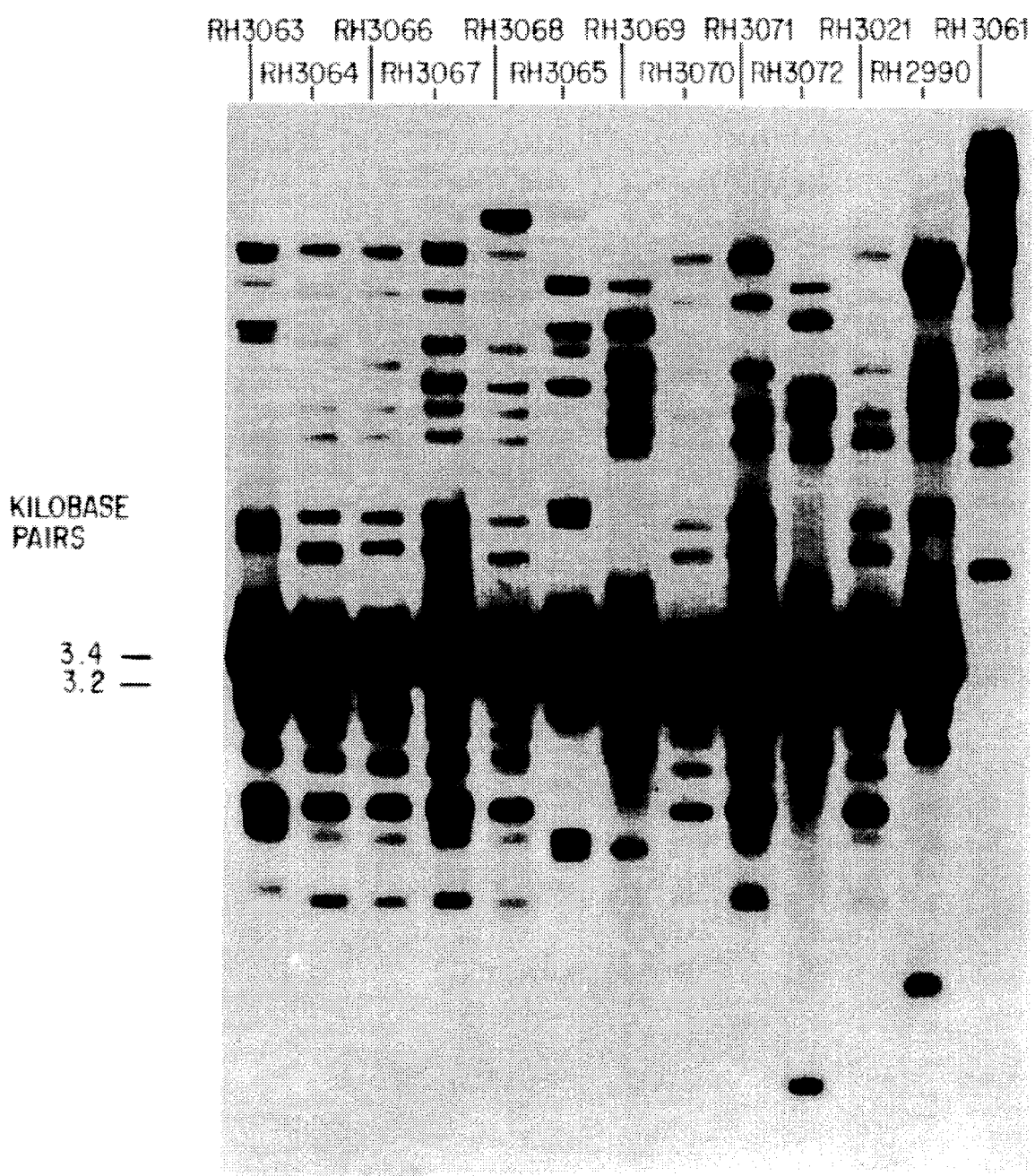
FIG. 6 shows the Pst I data for the same strains as in FIG. 5, with the same probe.
Figure 7:
FIG. 7 shows the Bgl II data for the same strains as in FIGS. 5 and 6, with the same probe.
Figure 8:
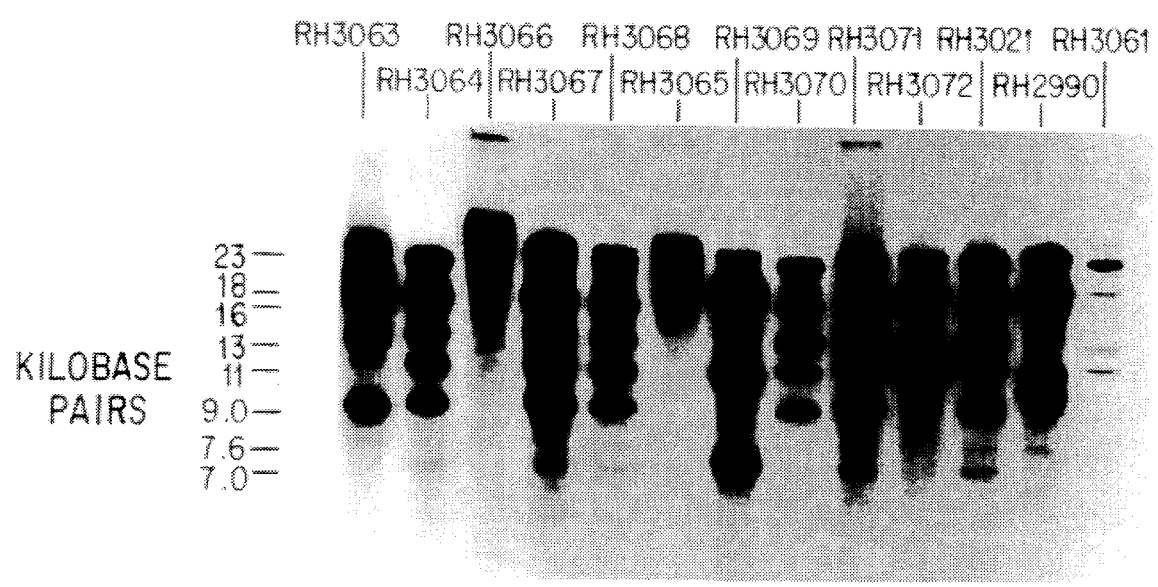
FIG. 8 shows the Sac I data for the same strains as in FIGS. 5–7, with the same probe.

The data shows there are two hybridization groups. Similar data is reported in the literature for *B. subtilis* (Seki et al, *International Journal of Systematic Bacteriology* 25:258–270 (1975)). These two groups can be represented by RH 3021 and RH 2990. When restriction endonuclease analysis of ribosomal RNA genes is carried out, EcoR I digests (FIG. 5) can be separated into two groups. The group represented by RH 3021 has two intensely hybridized fragments ( 2.15 and 2.1 KBP). The group represented by RH 2990 has two intensely hybridized fragments (2.6 and 2.5 KBP). The EcoR I data can be used to place *B. subtilis* strains in appropriate DNA—DNA hybridization groups. According to the DNA—DNA hybridization 70% rule, *B. subtilis* is actually two species. However, when the PST I data (FIG. 6) is considered, it is possible to think of the groups as two divergent populations related to a common ancestor or speciation event. The conclusion that *B. subtilis* is one species correlates with phenotypic data. The strains listed in Table 5 are identified as *B. subtilis* in Gordon, R. E et al "The Genus Bacillus" *Agriculture Handbook* No. 427, Agricultural Research Service, U.S. Dept. of Agriculture, Washington, D.C. pp. 36–41. Restriction analysis can provide data which is comparable to DNA—DNA hybridization data, or by selecting the proper enzyme, restrction analysis can adequately define species despite divergence. RH 3061 has lost PST I sites. However, ever, the EcoR I data suggests that the strain is *B. subtilis*. The same is concluded from the Bgl II data (FIG. 7) and Sac I data (FIG. 8).

EXAMPLE 3

Stability of the Restriction Analysis Pattern and Other *Bacillus polymyxa* Experiments

TABLE 7

Neotype strains of *B. subtilis* and *B. polymyxa*

| Species | RH | ACTT | NRRL | Comments |
|---|---|---|---|---|
| *B. subtilis* | 3021 | 6051 |  | neotype |
| *B. polymyxa* | 3074 | 842 |  | neotype |
| *B. polymyxa* | 3033 |  |  | asporogenous mutant derived from RH 3074 |
| *B. polymyxa* | 3062 |  | NRS-1105 | neotype |
| *B. polymyxa* | 3073 |  |  | asporogenous mutant derived from NRS-1105 |

*B. subtilis* and *B. polymyxa* can be distinguished by EcoR I data (FIG. 9), PST I data (FIG. 10) Bgl II data (FIG. 11, left) and Sac I data (FIG. 11, right). It can be concluded from the major differences in the PST I band patterns that *bacillus polymyxa* is in the wrong genus. While both species produce spores, they are not phenotypically similar. It is reassuring that the type strain of *B. polymyxa* from both culture collections, ATCC and NRRL have the same band patterns. The important data, however, is that the asporogenous mutants can be identified. It is very difficult, perhaps impossible, to identify Bacillus species if they fail to form spores.

EXAMPLE 4

Identification of a Bacterial Species in Mouse Tissue without Isolation

A Swiss mouse, *Mus musculus domesticus* (inbred strain), was inoculated intraperitoneally with 0.5 ml of a turbid suspension of *Streptococcus pneumoniae* RH 3077 (ATCC 6303). When the mouse became moribund, the heart, lungs, and liver were removed. High molecular weight DNA was isolated from these tissues, *S. pneumoniae* RH 3077 and Swiss mouse organs, and the procedure for restriction endonuclease analysis of rRNA genes was carried out using EcoR I to digest the DNAs. In addition to washing the filters in 3 X SSC, they were washed for 2×15 minute periods in 0.3 X SSC and 0.05% SDS. Autoradiography was carried out for 48 hr. The data (FIG. 12) shows that *S. pneumoniae* can be defined by seven hybridized fragments (17.0, 8.0, 6.0, 4.0, 3.3, 2.6 and 1.8 KBP). The bacterial cDNA probe hybridizes poorly to two mouse DNA fragments (14.0 and 6.8 KBP). Hybridized fragments signal the presence of *S. pneumoniae* in the infected tissues. All seven bands can be seen in the heart DNA extract. They are less intense in the liver DNA extract, but all can be seen in the autoradiograph. Only the 6.0 KBP band appears in the lung DNA extract. The lesser number of bacteria in the lungs can be explained by the mouse having septicemia rather then pneumonia. The lungs showed no consolidation at autopsy. In order to determine the sensitivity of the assay, bacterial DNA was diluted with mouse DNA and electrophoresed. All seven bands can be seen in the autoradiograph when 0.1 micrograms of bacterial DNA is used. The 17.0, 8.0 and 6.0 KBP bands can be seen with $10^{-3}$ µg of bacterial DNA. If the figure of $5 \times 10^{-3}$ µg DNA per $10^6$ *S. pneumoniae* cells is used (*Biochim Biophys Acta*, 26:68), $10^{-1}$ µg is equivalent to $2 \times 10^7$ cells. The present technique is thus useful for diagnosing infections at this level of sensitivity.

Figure 9:
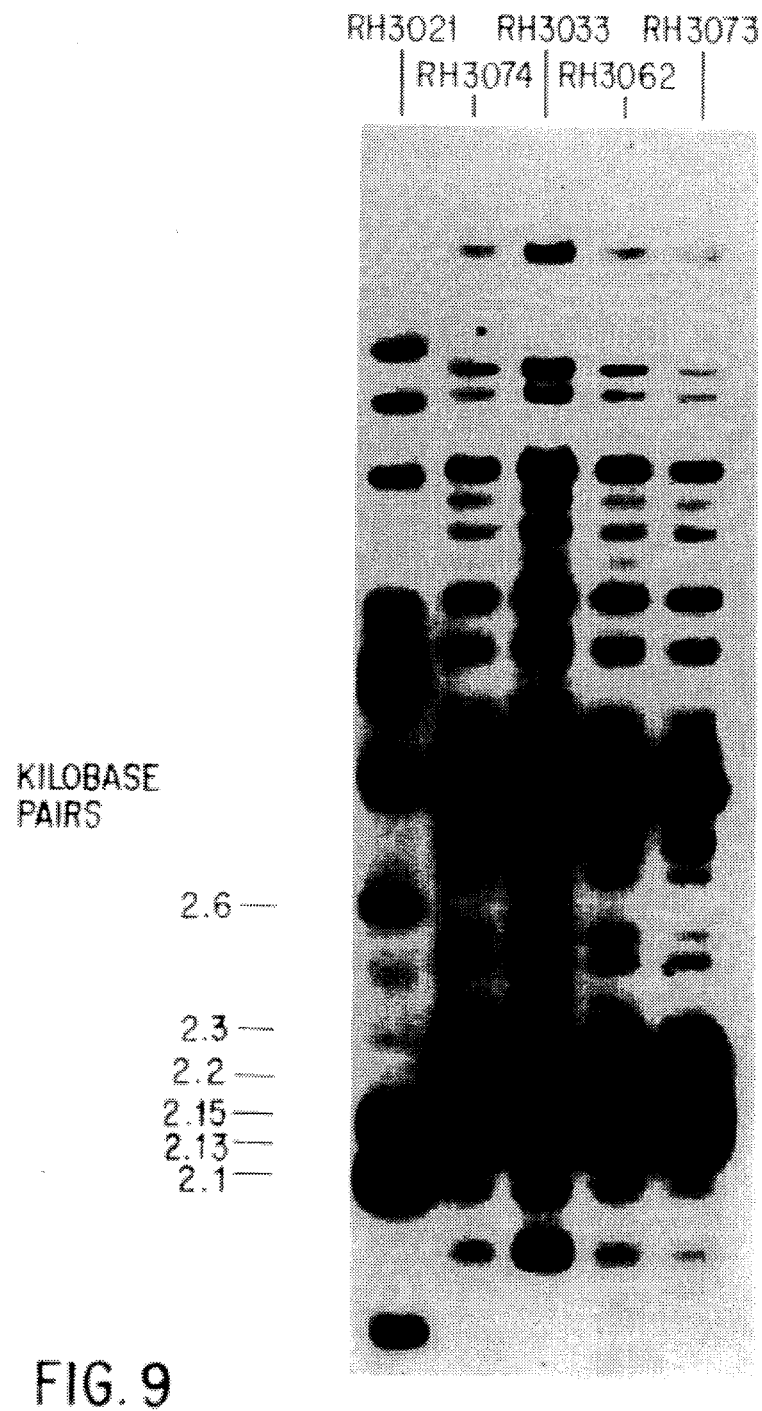
FIG. 9 shows the EcoR I restriction endonuclease digest of DNA isolated from *B. subtilis* and *B. polymyxa*, using cDNA to 16S and 23S rRNA from *E. coli* as the probe.
Figure 10:
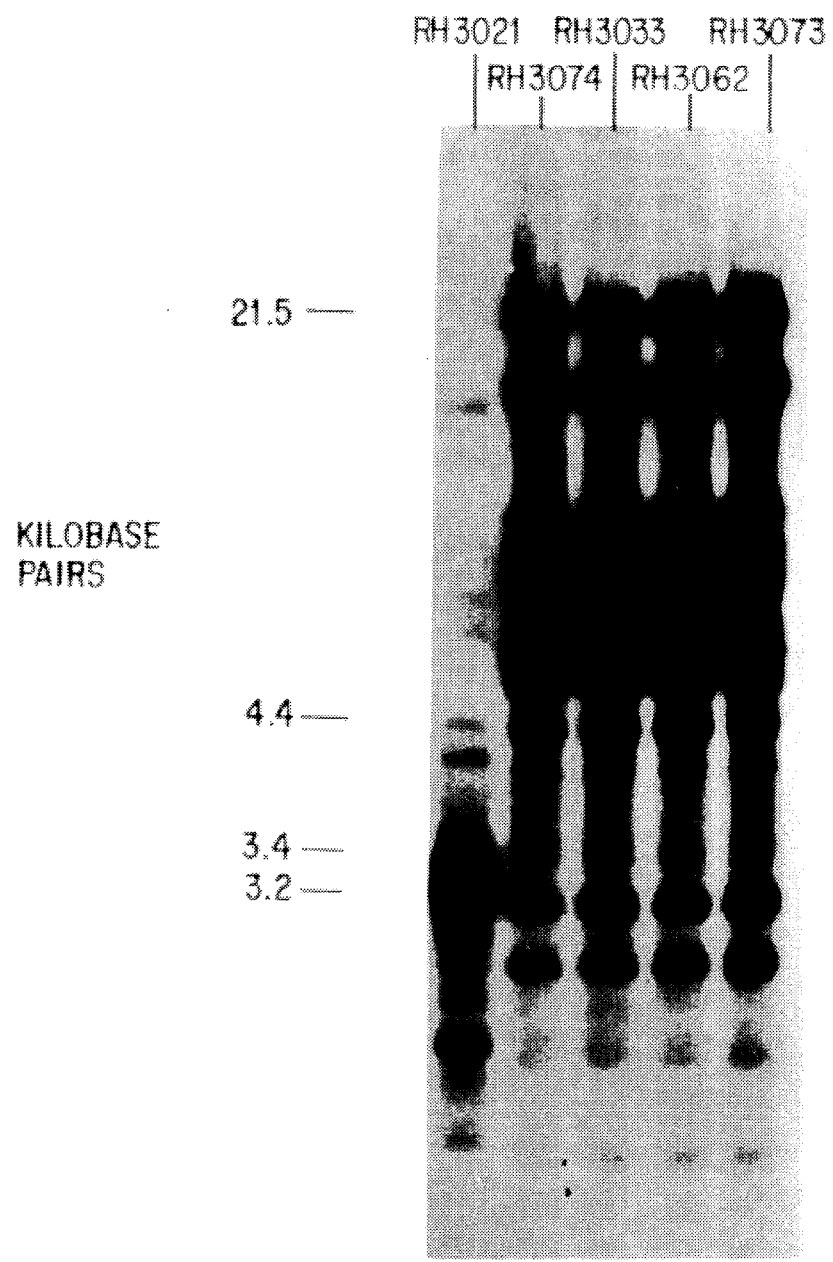
FIG. 10 shows the Pst I data for the same strains as in FIG. 9 with the same probe.

This Example also demonstrates that the bacterial probe hybridizes with mouse-specific EcoR I fragments (see FIG. 9, fragments having 14.0 and 6.8 KBP). These fragments correspond to EcoR I fragments detected by mouse 18S and 28S ribosomal RNA probe (FIG. 14 infra shows that the 6.8 KBP fragment contains the 28S rRNA sequences). The bacterial probe does not hybridize as well to mammalian ribosomal RNA gene sequences, so the bands are less intense, the system of bacterial probe and nuclear mammalian DNA is less sensitive, and selectivity for DNA from infecting prokaryotes is clearly demonstrated. In experiments where bacterial probe was hybridized to 10 µg digested bacterial DNA per lane, no hybridization to 10 µg digested human or mouse DNA per lane was detected on the autoradiographs when the bacterial bands were clearly seen.

EXAMPLES 5–8

Mammalian experiments

These examples illustrate that the concept of rRNA restriction analysis to identify organisms can be successfully applied not only to bacteria but to complex, eukaryotic organisms.

Figure 13:
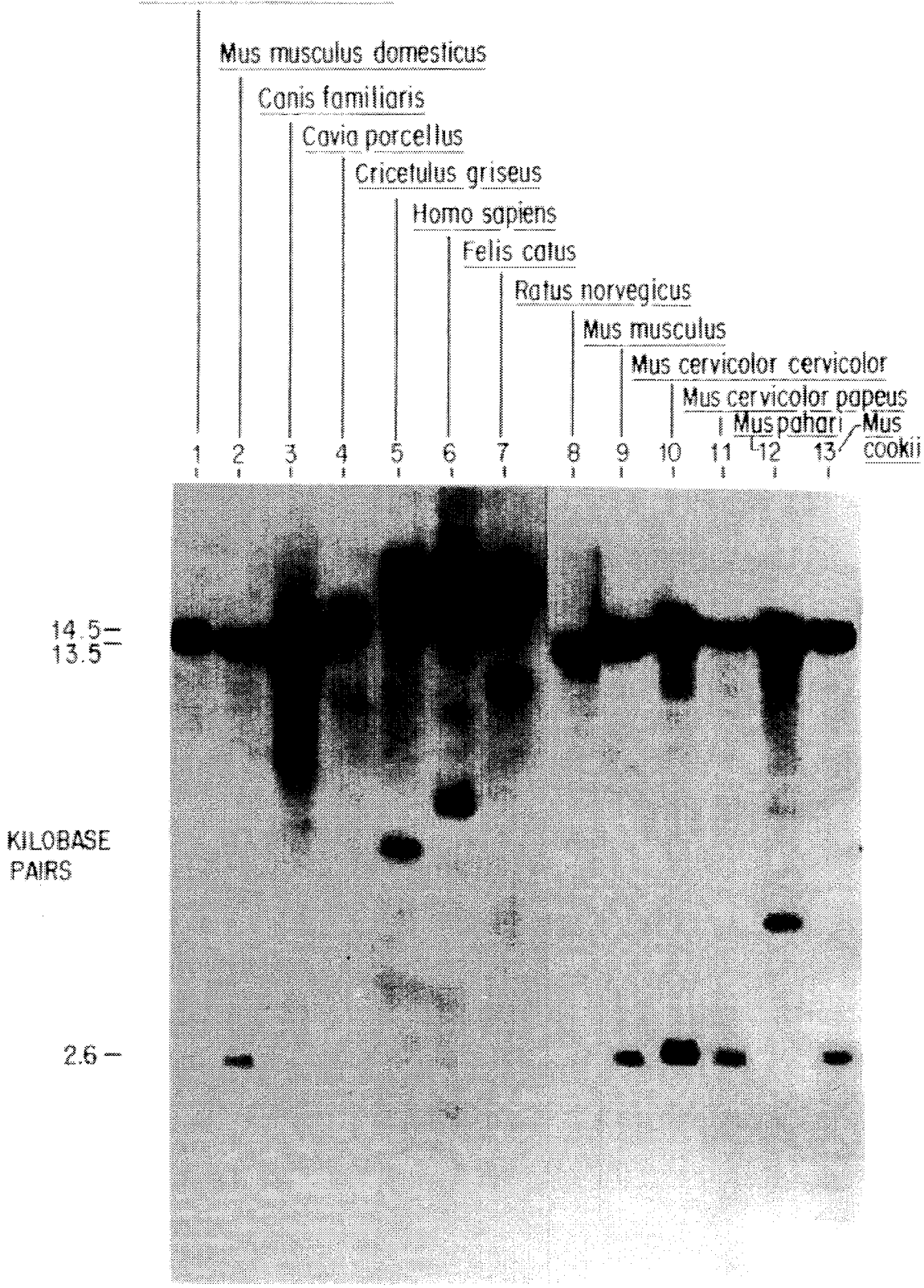
FIG. 13 shows the identification of a mouse species by comparing Pst I digests of DNA isolated from mammalian tissues, using cDNA to 18S and 28S rRNA from cytoplasmic ribosomes of *Mus musculus domesticus* (mouse).

FIG. 13 shows that mammalian genera can be recognized with Mus musculus domesticus 18S and 28S rRNA probe, and that several species of Mus can be distinguished. In this figure, the enzyme is PST I and the subjects and corresponding bands are as follows:

1. *Mus musculus melossinus* (mouse) 14.5, 13.5, 2.6
2. *Mus musculus domesticus* (mouse) 13.5, 2.6
3. *Canis familiaris* (dog) 12.0
4. *Cavia porcellus* (guinea pig) 17.0, 14.0, 13.0, 8.8, 5.7, 4.7, and one band less than 3.0
5. *Cricetulus griseus* (hamster) 25.0, 4.7
6. *Homo sapiens* (human) 15.0, 5.7
7. *Felis catus* (cat) 20.0, 9.7
8. *Ratus norvegicus* (rat) 12.5
9. *Mus musculus domesticus* (mouse) 13.5, 2.6
10. *Mus cervicolor cervicolor* (mouse) 14.0, 2.7
11. *Mus cervicolor papeus* (mouse) 13.5, 2.6
12. *Mus pahari* (mouse) 13.0, 3.7
13. *Mus cookii* (mouse) 13.5, 2.6

Figure 14:
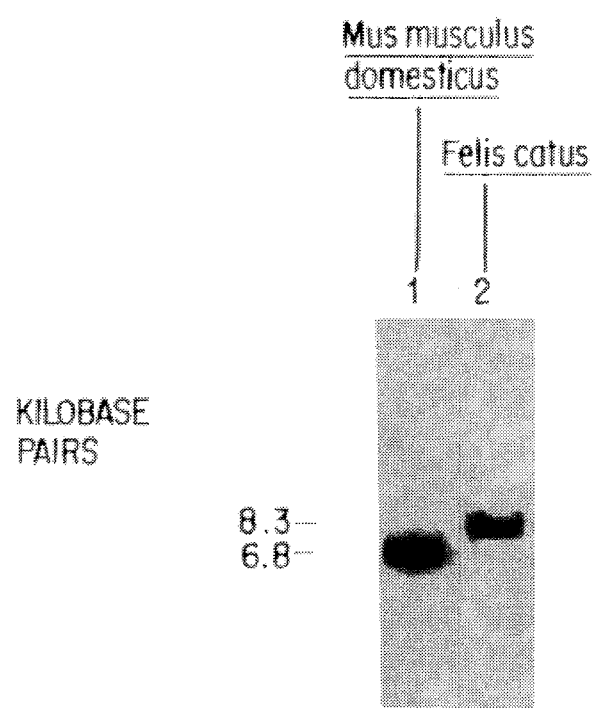
FIG. 14 shows the EcoR I digested DNA from mouse and cat tissues hybridized with *Mus musculus domesticus* 28S rRNA cDNA probe.

FIG. 14 shows that mouse and cat DNA can be distinguished by the 28S rRNA cDNA alone, and that the pattern of hybridized bands is dependent on the composition of the probe sequences. In FIG. 14 the enzyme is EcoR I, and the subjects and bands are as follows:

1. *Mus musculus domesticus* (mouse) 6.8 KBP
2. *Felis catus* (cat) 8.3 KBP

Figure 15:
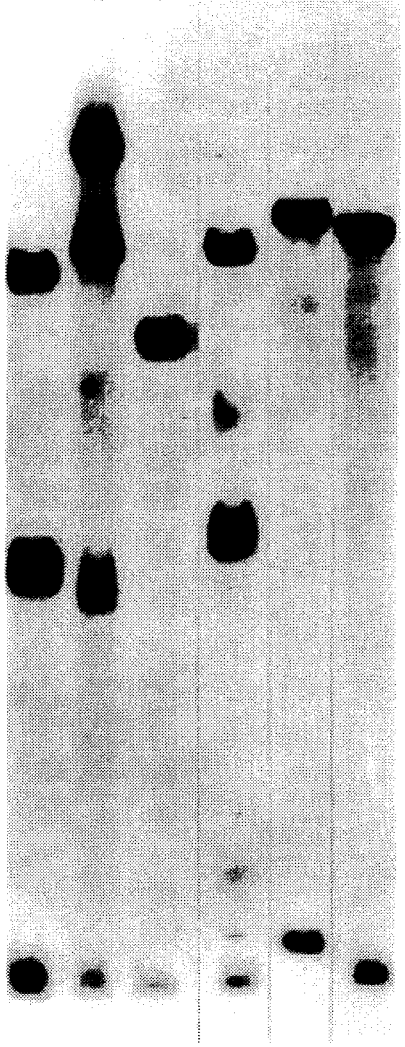
FIG. 15 shows Sac I digested DNA from mammalian tissues hybridized with *Mus musculus domesticus* 18S and 28S rRNA cDNA probe.

In FIG. 15 the enzyme is Sac I, and the subjects and bands are as follows:

1. *Erythrocebus patas* (patas monkey ) 8.5, 3.7, <3.0
2. *Ratus norvegicus* (rat) 25.0, 9,5, 3.6, <3.0
3. *Mus musculus domesticus* (mouse) 6.8, <3.0
4. *Felis catus* (cat) 9.5, 5.3, 4.0, <3.0, <3.0
5. *Homo sapiens* (human) 10.5, <3.0
6. *Macaca mulatta* (rhesus monkey) 9.8, <3.0 When FIG. 15 (Sac I digests) is compared to the other mammalian figures it can be seen the the hybridized pattern is enzyme specific.

Figure 16:
FIG. 16 shows EcoR I digested DNA from mammalian tissues and cell cultures hybridized with *Mus musculus domesticus* 18S and 28S rRNA cDNA probe.

FIG. 16 shows that primates can be distinguished. Cell cultures have bands in common with tissue from the species of origin, and different human cell cultures can be distinguished by additions and deletions of bands. In this figure, the enzyme is EcoR I, and the subjects and bands are as follows:

1. *Erythrocebus patas* (patas monkey ) >22.0, 11.0, 7.6, 2.6
2. *Macaca mulatta* (rhesus monkey) 22.0, 11.5, 7.6
3. *Homo sapiens* (human) >22.0, 22.0, 16.0, 8.1, 6.6
4. M 241/88 (langur monkey cell culture) 14.0, 7.2, 5.7
5. HeLa (human cell culture ) >8,1, 6.6
6. J96( human cell culture) >22.0, 22.0, 16.0, 11.0, 8.1, 6.6
7. AO (human cell culture) 22.0, 16.0, 8.1, 6.6
8. X-381 (rhesus monkey) 22.0, 11.5, 7.6

EXAMPLE 9

Use of an H4 Histone Gene Probe

A computer simulation of the identification and characterization of two animal species (sea urchin and mouse) was carried out using a conserved DNA sequence derived from the H4 histone gene.

The histone H4 gene sequence for sea urchin (Psammechinus miliaris) is shown below, where A, T, C, G, represent the known nucleotides, and N represent a presently unknown position (788 base pairs).

```
         10         20         30         40         50
   CAACATATTA GAGGAAGGGA GAGAGAGAGA GAGAGAGAGA GAGAGAGAGA
   GTTGTATAAT CTCCTTCCCT CTCTCTCTCT CTCTCTCTCT CTCTCTCTCT 60         70         80         90        100
   GGGGGGGGGG GAGGGAGAAT TGCCCAAAAC ACTGTAAATG TAGCGTTAAT
   CCCCCCCCCC CTCCCTCTTA ACGGGTTTTG TGACATTTAC ATCGCAATTA 110        120        130        140        150
   GAACTTTTCA TCTCATCGAC TGCGCGTGTA TAAGGATGAT TATAAGCTTT
   CTTGAAAAGT AGAGTAGCTG ACGCGCACAT ATTCCTACTA ATATTCGAAA 160        170        180        190        200
   TTTTCAATTT ACAGGCACTA CGTTACATTC AAATCCAATC AATCATTTGA
   AAAAGTTAAA TGTCCGTGAT GCAATGTAAG TTTAGGTTAG TTAGTAAACT 210        220        230        240        250
   ATCACCGTCG CAAAAGGCAG ATGTAAACTG TCAAGTTGTC AGATTGTGTG
   TAGTGGCAGC GTTTTCCGTC TACATTTGAC AGTTCAACAG TCTAACACAC 260        270        280        290        300
   CGCGGCCTCC AGTGAGCTAC CCACCGGGCC GTCGCGGAGG GGCGCACCTG
   GCGCCGGAGG TCACTCGATG GGTGGCCCGG CAGCGCCTCC CCGCGTGGAC
```

```
           310        320        330        340        350
TGCGGGAGGG GTCATCGGAG GGCGATCGAG CCTCGTCATC CAAGTCCGCA
ACGCCCTCCC CAGTAGCCTC CCGCTAGCTC GGAGCAGTAG GTTCAGGCGT 360        370        380        390        400
TACGGGTGAC AATACCCCCG CTCACCGGGA GGGTTGGTCA ATCGCTCAGC
ATGCCCACTG TTATGGGGGC GAGTGGCCCT CCCAACCAGT TAGCGAGTCG 410        420        430        440        450
GAAACGTCCA GTCGTCAGCA TCGCACTAAG ACTCTCTCTC AATCTCCATA
CTTTGCAGGT CAGCAGTCGT AGCGTGATTC TGAGAGAGAG TTAGAGGTAT 460        470        480        490        500
ATGTCAGGCC GTGGTAAAGG AGGCAAGGGG CTCGGAAAGG GAGGCGCCAA
TACAGTCCGG CACCATTTCC TCCGTTCCCC GAGCCTTTCC CTCCGCGGTT 510        520        530        540        550
GCGTCATCGC AAGGTCCTAC GAGACAACAT CCAGGGCATC ACCAAGCCTG
CGCAGTAGCG TTCCAGGATG CTCTGTTGTA GGTCCCGTAG TGGTTCGGAC 560        570        580        590        600
CAATCCGCCG ACTCNNNNNN NNNNNNNNNN NNNNNNGAAT CTCTGGTCTT
GTTAGGCGGC TGAGNNNNNN NNNNNNNNNN NNNNNNCTTA GAGACCAGAA 610        620        630        640        650
ATCTACGAGG AGACACGAGG GGTGCTGAAG GNNNNNNNNN NNNNNNNNNN
TAGATGCTCC TCTGTGCTCC CCACGACTTC CNNNNNNNNN NNNNNNNNNN 660        670        680        690        700
NNNNNNNNNN NNNNNNNNNN NNNNNNNNNN NNNNNNNNNN NNNNNNNNNN
NNNNNNNNNN NNNNNNNNNN NNNNNNNNNN NNNNNNNNNN NNNNNNNNNN 710        720        730        740        750
NNNNNNNNNN NNNNNNNNNN NNNNNNNNNN NNGGCCGAAC ACTGTACGGC
NNNNNNNNNN NNNNNNNNNN NNNNNNNNNN NNCCGGCTTG TGACATGCCG 760        770        780
TTCGGCGGCT AAGTGAAGCA GACTTGGCTA GAATAACG
AAGCCGCCGA TTCACTTCGT CTGAACCGAT CTTATTGC
```

The analogous mouse H4 gene sequence is shown below (968 base pairs):

```
           10         20         30         40         50
GAATTCTCCG AGGGACTTCG GCACCATAAT TAAGAAAATC GAAAATAAAA
CTTAAGAGGC TCCCTGAAGC CGTGGTATTA ATTCTTTTAG CTTTTATTTT 60         70         80         90         100
AAATAAAGGC TTGAGACTGT AAGGAACCGG TAGAGGGCAG AGAAGAGAAA
TTTATTTCCG AACTCTGACA TTCCTTGGCC ATCTCCCGTC TCTTCTCTTT 110        120        130        140        150
AGAAAAACAG GAAGATGATG CAACATCCAG AGCCCGGATA ATTTAGAAAG
TCTTTTTGTC CTTCTACTAC GTTGTAGGTC TCGGGCCTAT TAAATCTTTC 160        170        180        190        200
GTTCCCGCCC GCGCGCTTTC AGTTTTCAAT CTGGTCCGAT CCTCTCATAT
CAAGGGCGGG CGCGCGAAAG TCAAAAGTTA GACCAGGCTA GGAGAGTATA 210        220        230        240        250
ATTAGTGGCA CTCCACCTCC AATGCCTCAC CAGCTGGTGT TTCAGATTAC
TAATCACCGT GAGGTGGAGG TTACGGAGTG GTCGACCACA AAGTCTAATG 260        270        280        290        300
ATTAGCTATG TCTGGCAGAG GAAAGGGTGG AAAGGGTCTA GGCAAGGGTG
TAATCGATAC AGACCGTCTC CTTTCCCACC TTTCCCAGAT CCGTTCCCAC 310        320        330        340        350
GCGCCAAGCG CCATCGCAAA GTCTTGCGTG ACAACATCCA GGGTATCACC
CGCGGTTCGC GGTAGCGTTT CAGAACGCAC TGTTGTAGGT CCCATAGTGG 360        370        380        390        400
AAGCCCGCCA TCCGCCGCCT GGCTCGGCGC GGTGGGGTCA AGCGCATCTC
TTCGGGCGGT AGGCGGCGGA CCGAGCCGCG CCACCCCAGT TCGCGTAGAG 410        420        430        440        450
CGGCCTCATC TACGAGGAGA CCCGTGGTGT GCTGAAGGTG TTCCTGGAGA
GCCGGAGTAG ATGCTCCTCT GGGCACCACA CGACTTCCAC AAGGACCTCT
```

-continued

```
       460        470        480        490        500
ACGTCATCCG CGACGCAGTC ACCTACACCG AGCACGCCAA GCGCAAGACC
TGCAGTAGGC GCTGCGTCAG TGGATGTGGC TCGTGCGGTT CGCGTTCTGG 510        520        530        540        550
GTCACCGCTA TGGATGTGGT GTACGCTCTC AAGCGCCAGG GCCGCACCCT
CAGTGGCGAT ACCTACACCA CATGCGAGAG TTCGCGGTCC CGGCGTGGGA 560        570        580        590        600
CTACGGCTTC GGAGGCTAGA CGCCGCCGCT TCAATTCCCC CCCCCCCCCC
GATGCCGAAG CCTCCGATCT GCGGCGGCGA AGTTAAGGGG GGGGGGGGGG 610        620        630        640        650
ATCCCTAACG GCCCTTTTTA GGGCCAACCA CAGTCTCTTC AGGAGAGCTG
TAGGGATTGC CGGGAAAAAT CCCGGTTGGT GTCAGAGAAG TCCTCTCGAC 660        670        680        690        700
ACACTGACTT GGGTCGTACA GGTAATAACC GCGGGTTTAG GACTCACGCT
TGTGACTGAA CCCAGCATGT CCATTATTGG CGCCCAAATC CTGAGTGCGA 710        720        730        740        750
ACTAGGTGTT CCGCTTTTAG AGCCATCCAC TTAAGTTTCT ATACCACGGC
TGATCCACAA GGCGAAAATC TCGGTAGGTG AATTCAAAGA TATGGTGCCG 760        770        780        790        800
GGATAGATAG CATCCAGCAG GGTCTGCTCA CACTGGGAAT TTTAATTCCT
CCTATCTATC GTAGGTCGTC CCAGACGAGT GTGACCCTTA AAATTAAGGA 810        820        830        840        850
ACTTAGGGTG TGAGCTGGTT GTCAGGTCAA GAGACTGGCT AAGATTTTCT
TGAATCCCAC ACTCGACCAA CAGTCCAGTT CTCTGACCGA TTCTAAAAGA 860        870        880        890        900
TTAGCTCGTT TGGAGCAGAA TTGCAATAAG GAGACCCTTT GGATGGGATG
AATCGAGCAA ACCTCGTCTT AACGTTATTC CTCTGGGAAA CCTACCCTAC 910        920        930        940        950
ACCTATGTCC ACACATCAAA TGGCTATGTG GCTGTGTCCC TGTGTTTCCA
TGGATACAGG TGTGTAGTTT ACCGATACAC CGACACAGGG ACACAAAGGT

960
ATGAGTGGCT GTGCTTGA
TACTCACCGA CACGAACT
```

The region of homology for both aforementioned sequences is shown below, where asterisks denote not homologous portions. Within the region shown, the first 118 base pairs have 80.5% homology and are used as a conserved DNA sequence probe in this example (sea urchin (top) base positions 449 to 567, mouse (bottom) base positions 257 to 375):

Restriction endonuclease cleavage sites were determined from the two sequences. A list of cleavage sites for the sea urchin and mouse sequences is shown below. Numbers indicate the 5' side of the cleavage site, unless site name is in brackets, which indicates that only the recognition site is known.

```
        *   *  * *      * *  *  *    *   *   *  *           *
449 TAATGTCAGGCCGTGGTAAAGG-AGGCAA-GGGGCTCGG-AAAGGGAGGCGCCAAGCGTC
257 TA-TGTCTGGCAGAGG-AAAGGGTGG-AAAGGGTCTAGGCAA-GGGTGGCGCCAAGCGCC

*   * * *          *         *  *         *    |* *
    ATCGCAAGGTCCTACGAGACAACATCCAGGGCATCACCAAGCCTGCAATCCGCCGACT|-C
    ATCGCAAAGTCTTGCGTGACAACATCCAGGGTATCACCAAGCCCGCCATCCGCCGCCT|GG

* *    * * * *                         *  * *   *
    NNNNNNNNNNNNNNNNNNNNNNNGAATCTCTGGTCTT-ATCTACGAGGAGACACGAGGG-G
    CTCGGCGCGGTGGGGTCAAGCG-CATCTCCGG-CCTCATCTACGAGGAGACCCG-TGGTG

TGCTGAAGGNNNNNNNNNNNNNNNNNNNNNNNNNNNNNNNNNNNNNNNNNNNNNNNNNNNN
    TGCTGAAGGTGTTCCTGGAGAACGTCATCCGCGACGCAGTCACCTACACCGAGCACGCCA

*  *  *
    NNNNNNNNNNNNNNNNNNNNNNNNNNNNNNNNNNNNNNNNNNNNNNNNNNNGGCCG-AAC-
    AGCGCAAGACCGTCACCGCTATGGATGTGGTGTACGCTCTCAAGCGCCAGGGCCGCACCC

*  **       *      * * *  *  *  *  * *   * *  *
    ACTGTACGGCTTCGGCGGCTAAGTGAAGCAGAC--TTGGCTA 780
    TCT--ACGGCTTCGGAGGCTA---GACGCCGCCGCTT--CAA 584
```

% = 84.503
P(342, 289) = .000E+00  E = .000

| Sequence | Appears at position | | | | | |
|---|---|---|---|---|---|---|
| | SEA URCHIN | | | | | |
| AcyI (GPCGQC) | 495 | | | | | |
| AluI (AGCT) | 147 | 267 | | | | |
| AsuI (GGNCC) | 277 | 514 | | | | |
| AvaII (GGLCC) | 514 | | | | | |
| CauII (CCMGG) | 276 | 377 | | | | |
| DdeI (CTNAG) | 396 | 427 | | | | |
| DpnI (GATC) | 326 | | | | | |
| EcoRI* (PPATQQ) | 184 | | | | | |
| EcoRII (CCLGG) | 531 | | | | | |
| Fnu4HI (GCNGC) | 254 | | | | | |
| FnuDII (CGCG) | 125 | 253 | 285 | | | |
| FokI (GGATG) | 148 | | | | | |
| FokI (CATCC) | 324 | 515 | | | | |
| HaeII (PGCGCQ) | 498 | | | | | |
| HaeIII (GGCC) | 256 | 279 | 459 | | | |
| HsaI (GCGTC) | 491 | | | | | |
| HsiCI (GGQPCC) | 494 | | | | | |
| HsiJII (GPGCQC) | 483 | | | | | |
| HhaI (GCGC) | 125 | 253 | 295 | 497 | | |
| HindIII (AAGCTT) | 145 | | | | | |
| HinfI (GANTC) | 200 | 431 | 561 | | | |
| HpaII (CCGG) | 275 | 376 | | | | |
| HphI (GGTGA) | 368 | | | | | |
| HphI (TCACC) | 195 | 365 | 532 | | | |
| MboI (GATC) | 324 | | | | | |
| MnlI (CCTC) | 267, | 342 | | | | |
| MnlI (GAGG) | 4 | 42 | 54 | 280 | 299 | 311 |
| | 372 | 463 | 484 | | | |
| NarI (GGCGCC) | 495 | | | | | |
| NspBII (GCMGC) | 256 | | | | | |
| PvuI (CCATCG) | 327 | | | | | |
| ScrFI (CCNGG) | 276 | 377 | 533 | | | |
| SfaNI (GCATC) | 409 | 527 | | | | |
| TaqI (TCGA) | 117 | 327 | | | | |
| | MOUSE | | | | | |
| AcyI (GPCGQC) | 302 | 571 | | | | |
| AflII (CTTAAG) | 731 | | | | | |
| AluI (AGCT) | 234 | 256 | 648 | 815 | 855 | |
| AsuI (GGNCC) | 184 | 540 | 611 | 622 | | |
| AvaII (GGLCC) | 184 | | | | | |
| BssHII (GCGCGC) | 162 | | | | | |
| CauII (CCMGG) | 135 | | | | | |
| DdeI (CTNAG) | 803 | 840 | | | | |
| DpnI (GATC) | 190 | | | | | |
| [EcoB] (AGCANNNNNNNTCA) | 766 | | | | | |
| [EcoP1] (AGACC) | 418 | 496 | 882 | | | |
| [EcoP1] (GGTCT) | 285 | 771 | | | | |
| [EcoP15] (CAGCAG) | 765 | | | | | |
| EcoRI (GAATTC) | 2 | | | | | |
| EcoRI* (PPATQQ) | 4 | 790 | 845 | | | |
| EcoRII (CCLGG) | 338 | 368 | 443 | 536 | | |
| Fnu4HI (GCNGC) | 366 | 543 | 574 | 577 | | |
| FnuDII (CGCG) | 162 | 164 | 380 | 461 | 682 | |
| FokI (GGATG) | 526 | 905 | 910 | | | |
| FokI (CATCC) | 111 | 322 | 346 | 442 | 587 | 711 | 748 |
| HaeII (PGCGCQ) | 305 | 312 | 537 | | | |
| HaeIII (GGCC) | 404 | 542 | 612 | 624 | | |
| HsaI (CACGC) | 472 | 579 | | | | |
| HsiAI (GLGCLC) | 485 | | | | | |
| HsiCI (GGQPCC) | 21 | 301 | | | | |
| HsiJII (GPGCQC) | 135 | | | | | |
| HhaI (GCGC) | 164 | 166 | 304 | 311 | 380 | 395 |
| | 494 | 536 | | | | |
| HinfI (GANTC) | 692 | | | | | |
| HpaII (CCGG) | 78 | 135 | 401 | | | |
| HphI (TCACC) | 220 | 339 | 462 | 495 | | |
| MboI (GATC) | 188 | | | | | |
| MboII (GAAGA) | 105 | 124 | | | | |
| MboII (TCTTC) | 629 | | | | | |
| MnlI (CCTC) | 202 | 227 | 236 | 415 | 559 | |
| MnlI (GAGG) | 3 | 76 | 261 | 407 | 555 | |
| NarI (GGCGCC) | 302 | | | | | |
| NspBII (GCMGC) | 368 | 545 | 576 | 579 | | |
| PvuII (CAGCTG) | 234 | | | | | |
| RsaI (GTAC) | 523 | 668 | | | | |

| Sequence | Appears at position | | | | |
|---|---|---|---|---|---|
| SacII (CCGCGG) | 683 | | | | |
| ScrFI (CCNGG) | 135 | 340 | 370 | 445 | 538 |
| SfaNI (GATGC) | 127 | | | | |
| SfaNI (GCATC) | 385 | 751 | | | |
| TaqI (TCGA) | 40 | | | | |
| Tth111I (GACNNNGTC) | 466 | | | | |
| Tth111II (TGQTTG) | 953 | | | | |
| XmnI (GAANNNNTTC) | 439 | | | | |

The sea urchin and mouse sequences are compared with Hha I (GCGC) and the described probe sequence. The sea urchin sequence has cleavage sites at positions 295 and 497, thus creating a 202 bp fragment, which, if denatured, would hybridize with the probe sequence. Hha I (GCGC) sites in the mouse sequence, 166, 304, 311 and 380, indicate that fragments of 69 and 138 could be detected with the probe sequence.

Thus the genetic characterization for sea urchin is
202
while that for mouse is
69
138

EXAMPLE 10

Use of trp D Gene of the Tryptophan Operon as a Probe

The same type of computer simulation as in Example 9 was carried out using trp D gene as a probe. This allows the conclusion that *E. coli* and *Salmonella typhimurium* can be distinguished by restriction fragments containing a conserved sequence.

The *E. coli* trp D gene with 684 bp's is shown below:

```
              10         20         30         40         50
         GAAGCCGACG AAACCCGTAA CAAAGCTCGC GCCGTACTGC GCGCTATTGC
         CTTCGGCTGC TTTGGGCATT GTTTCGAGCG CGGCATGACG CGCGATAACG 60         70         80         90        100
         CACCGCGCAT CATGCACAGG AGACTTTCTG ATGGCTGACA TTCTGCTGCT
         GTGGCGCGTA GTACGTGTCC TCTGAAAGAC TACCGACTGT AAGACGACGA 110        120        130        140        150
         CGATAATATC GACTCTTTTA CGTACAACCT GGCAGATCAG TTGCGCAGCA
         GCTATTATAG CTGAGAAAAT GCATGTTGGA CCGTCTAGTC AACGCGTCGT 160        170        180        190        200
         ATGGGCATAA CGTGGTGATT TACCGCAACC ATATACCGGC GCAAACCTTA
         TACCCGTATT GCACCACTAA ATGGCGTTGG TATATGGCCG CGTTTGGAAT 210        220        230        240        250
         ATTGAACGCT TGGCGACCAT GAGTAATCCG GTGCTGATGC TTTCTCCTGG
         TAACTTGCGA ACCGCTGGTA CTCATTAGGC CACGACTACG AAAGAGGACC 260        270        280        290        300
         CCCCGGTGTG CCGAGCGAAG CCGGTTGTAT GCCGGAACTC CTCACCCGCT
         GGGGCCACAC GGCTCGCTTC GGCCAACATA CGGCCTTGAG GAGTGGGCGA 310        320        330        340        350
         TGCGTGGCAA GCTGCCCATT ATTGGCATTT GCCTCGGACA TCAGGCGATT
         ACGCACCGTT CGACGGGTAA TAACCGTAAA CGGAGCCTGT AGTCCGCTAA 360        370        380        390        400
         GTCGAAGCTT ACGGGGGCTA TGTCGGTCAG GCGGGCGAAA TTCTCCACGG
         CAGCTTCGAA TGCCCCCGAT ACAGCCAGTC CGCCCGCTTT AAGAGGTGCC 410        420        430        440        450
         TAAAGCCTCC AGCATTGAAC ATGACGGTCA GGCGATGTTT GCCGGATTAA
         ATTTCGGAGG TCGTAACTTG TACTGCCAGT CCGCTACAAA CGGCCTAATT 460        470        480        490        500
         CAAACCCGCT GCCGGTGGCG CGTTATCACT CGCTGGTTGG CAGTAACATT
         GTTTGGGCGA CGGCCACCGC GCAATAGTGA GCGACCAACC GTCATTGTAA 510        520        530        540        550
         CCGGCCGGTT TAACCATCAA CGCCCATTTT AATGGCATGG TGATGGCAGT
         GGCCGGCCAA ATTGGTAGTT GCGGGTAAAA TTACCGTACC ACTACCGTCA 560        570        580        590        600
         ACGTCACGAT GCGGATCGCG TTTGTGGATT CCAGTTCCAT CCGGAATCCA
         TGCAGTGCTA CGCCTAGCGC AAACACCTAA GGTCAAGGTA GGCCTTAGGT
```

```
                  610        620        630        640        650
            TTCTCACCAC CCAGGGCGCT CGCCTGCTGG AACAAACGCT GGCCTGGGCG
            AAGAGTGGTG GGTCCCGCGA GCGGACGACC TTGTTTGCGA CCGGACCCGC 660        670        680
            CAGCATAAAC TAGAGCCAGC CAACACGCTG CAA
            GTCGTATTTG ATCTCGGTCG GTTGTGCGAC GTT
```

The trp D gene, 683 base pairs, for *S. typhimurium* is shown below:

```
                  10         20         30         40         50
            GAAGCCGATG AAACCCGTAA TAAAGCGCGC GCCGTATTGC GTGCTATCGC
            CTTCGGCTAC TTTGGGCATT ATTTCGCGCG CGGCATAACG CACGATAGCG 60         70         80         90        100
            CACCGCGCAT CATGCACAGG AGACCTTCTG ATGGCTGATA TTCTGCTGCT
            GTGGCGCGTA GTACGTGTCC TCTGGAAGAC TACCGACTAT AAGACGACGA 110        120        130        140        150
            CGATAACATC GACTCGTTCA CTTGGAACCT GGCAGATCAG CTACGAACCA
            GCTATTGTAG CTGAGCAAGT GAACCTTGGA CCGTCTAGTC GATGCTTGGT 160        170        180        190        200
            ACGGTCATAA CGTGGTGATT TACCGTAACC ATATTCCGGC GCAGACGCTT
            TGCCAGTATT GCACCACTAA ATGGCATTGG TATAAGGCCG CGTCTGCGAA 210        220        230        240        250
            ATCGATCGCC TGGCGACAAT GAAAAATCCT GTGCTAATGC TCTCCCCCGG
            TAGCTAGCGG ACCGCTGTTA CTTTTTAGGA CACGATTACG AGAGGGGGCC 260        270        280        290        300
            CCCGGGTGTT CCCAGCGAGG CAGGTTGTAT HCCGGAGCTG CTGACCCGAC
            GGGCCCACAA GGGTCGCTCC GTCCAACATA CGGCCTCGAC GACTGGGCTG 310        320        330        340        350
            TACGCGGCAA GTTACCGATC ATCGGCATTT GTCTGGGGCA TCAGGCGATT
            ATGCGCCGTT CAATGGCTAG TAGCCGTAAA CAGACCCCGT AGTCCGCTAA 360        370        380        390        400
            GTCGAAGCTT ACGGCGGTTA CGTCGGTCAG GCGGGAGAAA TCCTGCATGG
            CAGCTTCGAA TGCCGCCAAT GCAGCCAGTC CGCCCTCTTT AGGACGTACC 410        420        430        440        450
            CAAAGCCTCC AGCATTGAGC ATGACGGTCA GGCGATGTTC GCCGGGCTCG
            GTTTCGGAGG TCGTAACTCG TACTGCCAGT CCGCTACAAG CGGCCCGAGA 460        470        480        490        500
            CGAATCCGCT ACCGGTCGCG CGTTATCATT CGCTGGTCGG CAGTAATGTT
            GCTTAGGCGA TGGCCAGCGC GCAATAGTAA GCGACCAGCC GTCATTACAA 510        520        530        540        550
            CCTGCCGGGC TGACCATTAA CGCCCATTTC AACGGCATGG TGATGGCGGT
            GGACGGCCCG ACTGGTAATT GCGGGTAAAG TTGCCGTACC ACTACCGCCA 560        570        580        590        600
            ACGTCATGAT GCGGATCGCG TTTGCGGTTT TCAATTTCAT CCCGAGTCCA
            TGCAGTACTA CGCCTAGCGC AAACGCCAAA AGTTAAAGTA GGGCTCAGGT 610        620        630        640        650
            TCCTGACGAC AGAGGGCGCG CGTCTACTGG AGCAAACATT AGCCTGGGCG
            AGGACTGCTG TGTCCCGCGC GCAGATGACC TCGTTTGTAA TCGGACCCGC 660        670        680
            CTGGCGAAGC TGGAACCGAC CAACACCCTA CAG
            GACCGCTTCG ACCTTGGCTG GTTGTGGGAT GTC
```

Two homology regions between both sequences were next established, where the upper sequence is for *E. coli* and the lower one for *S. typhimurium*:

Region I

```
         **    *       *                  *          *         **     *  *   **
452  AAACCCGCTGCCGGTGGCGCGTTATCACTCGCTGGTTGGCAGTAACATTCC-GGCCGG-T
453  AA-TCCGCTACCGGTCGCGCGTTATCATTCGCTGGTCGGCAGTAATGTTCCTGCC-GGGC

*  *        *           *  *                      *          *
     TTAACCATCAACGCCCATTTTAATGGCATGGTGATGGCAGTACGTCACGATGCGGATCGC
     TGA-CCATTAACGCCCATTTCAACGGCATGGTGATGGCGGTACGTCATGATGCGGATCGC

*   **    *  *  *          *   *     *   *   *            *   *   *
     /GTTTGTGG-ATTGCAGTTCCATCCGGAATCCATTCTCACCACCCAGGGCGCTCGGCTGCT
     GTTTGCGGTTTTC-AATTTCATCCCGAGTCCATCCTGACGACACAGGGCGCGCGTCTACT

*    ** *              ** **   *   *   *  * * *        *   *
     GGAACAAACGCTGGCCTGGGCGC-AGCATAAACTAGAGCC-AGCCAACACGCTGCA       682
     GGAGCAAACATTAGCCTGGGCGCTGGC-GAAGCTGGAACCGACC-AACACCCTACA       682
```

% = 78.390
P(236, 185) = .000E+00  E = .000

Region II

```
           *          **  **    *    **        *       *         *
1    GAAGCCGACGAAACCCGTAA-CAA-AGCTCGCGCCGTACTGCGCGCTATTGCCACCGCGC
1    GAAGCCGATGAAACCCGTAATAAAGCGCGCGC--CGTATTGCGTGCTATCGCCACCGCGC

*   *                *                      *           *
     ATCATGCACAGGAGAC-TTTCTGATGGCTGACATTCTGCTGCTCGATAATATCGACTC-T
     ATCATGCACAGGAGACCTT-CTGATGGCTGATATTCTGCTGCTCGATAACATCGACTCGT

**   **  *  *  *            *  *    *   *   **    *
     TTTAC--GTACAACCTGGCAGATCAGTTGCGCAGC-AATGGG-CATAACGTGGTGATTTA
     T-CACTTGGA-ACC-TGGCAGATCAGCTACG-AACCAA-CGGTCATAACGTGGTGATTTA

*         *            *  *   *    * *   *     *    ** *
     CCGCAACCATATACCGGCGCAAAC-CTTAATTGAACGC-TTGGCGACCATGAGTAA-TCC
     CCGTAACCATATTCCGGCGCAGACGCTTA--TCGATCGCCTGG-CGACAATGA-AAAATCC

*         *       * * *   *       *   *     **   *  * **  *   *
     GGTGCTGATGCT-TTCTCCTGGCCCCGG-TGT-GCC-GAGCGAAGCCGGTTGTATGCCGG
     TGTGCTAATGCTCTCC-CCCGGCCC-GGGTGTTCCCAGCG--AGGCAGGTTGTATGCCGG

*   *   *        *   **   **       *  *  *  *          *   ** *
     AACTCCTCACCCG-CT-TGCGTGGCAAGCTGCCCATTATTGGCATTTGCCT-CGGACATC
     AGCTGCTGACCCGACTACGCG--GCAAGTTACCGATCATCGGCATTTGTCTGGGG-CATC

*  ** *                   *        *    *    *   *
     AGGCGATTGTCGAAGCTTACGG-GGGCTATGTCGGTCAGGCGGGCGAAATTCTCCACGG-
     AGGCGATTGTCGAAGCTTACGGCGG-TTACGTCGGTCAGGCGGGAGAAATCCTGCATGGC

*  *               *                    *
     TAAAGCCTCCAGCATTGAACATGACGGTCAGGCGATGTTTGCCGG                 445
     AAA-GCCTCCAGCATTGAGCATGACGGTCAGGCGATGTTCGCCGG                 445
```

% = 80.215
P(465, 373) = .000E+00  E = .000

Restriction sites in both sequences are shown as follows:

| | *E. coli* | | | | | | |
|---|---|---|---|---|---|---|---|
| HpaII (CCGG) | 187 | 229 | 254 | 272 | 283 | 443 | 463 | 502 |
| | 506 | 592 | | | | | | |
| HphI (GGTGA) | 177 | 552 | | | | | | |
| HphI (TCACC) | 285 | 597 | | | | | | |
| MboI (GATC) | 135 | 564 | | | | | | |
| | *S. typhimurium* | | | | | | |
| HpaII (CCGG) | 187 | 248 | 253 | 283 | 443 | 463 | 506 |
| HphI (GGTGA) | 177 | 552 | | | | | |
| MboI (GATC) | 135 | 204 | 317 | 564 | | | |
| MnlI (CCTC) | 417 | | | | | | |

The *E. coli* sequence has Mbo I (GATC) sites at 135 and 564. There is a 429 bp fragment that can be detected by both Region 1 and 2 probes. The same enzyme has sites at 135, 204, 317, and 564 in the *S. typhimurium* sequence. A probe of the two homology regions would detect fragments of 69, 113 and 247 bp.

Thus the identifying genetic characterization for *E. coli* with this probe and enzyme is

429 whereas that for *S. typhimurium* is

69

113

247

EXAMPLE 11

Use of α-Fetoprotein Gene as a Probe

This example shows the use of a region of homology in the α-fetoprotein gene sequence of human and rat, and the endonuclease MnlI (GAGG).

The human α-fetoprotein message cDNA (1578 bp's) is as follows:

```
           10         20         30         40         50
    AGCTTGGCAT AGCTACCATC ACCTTTACCC AGTTTGTTCC GGAAGCCACC
    TCGAACCGTA TCGATGGTAG TGGAAATGGG TCAAACAAGG CCTTCGGTGG 60         70         80         90        100
    GAGGAGGAAG TGAACAAAAT GACTAGCGAT GTGTTGGCTG CAATGAAGAA
    CTCCTCCTTC ACTTGTTTTA CTGATCGCTA CACAACCGAC GTTACTTCTT 110        120        130        140        150
    AAACTCTGGC GATGGGTGTT TAGAAAGCCA GCTATCTGTG TTTCTGGATG
    TTTGAGACCG CTACCCACAA ATCTTTCGGT CGATAGACAC AAAGACCTAC 160        170        180        190        200
    AAATTTGCCA TGAGACGGAA CTCTCTAACA AGTATGGACT CTCAGGCTGC
    TTTAAACGGT ACTCTGCCTT GAGAGATTGT TCATACCTGA GAGTCCGACG 210        220        230        240        250
    TGCAGCCAAA GTGGAGTGGA AAGACATCAG TGTCTGCTGG CACGCAAGAA
    ACGTCGGTTT CACCTCACCT TTCTGTAGTC ACAGACGACC GTGCGTTCTT 260        270        280        290        300
    GACTGCTCCG GCCTCTGTCC CACCCTTCCA GTTTCCAGAA CCTGCCGAGA
    CTGACGAGGC CGGAGACAGG GTGGGAAGGT CAAAGGTCTT GGACGGCTCT 310        320        330        340        350
    GTTGCAAAGC ACATGAAGAA AACAGGGCAG TGTTCATGAA CAGGTTCATC
    CAACGTTTCG TGTACTTCTT TTGTCCCGTC ACAAGTACTT GTCCAAGTAG 360        370        380        390        400
    TATGAAGTGT CAAGGAGGAA CCCCTTCATG TATGCCCCAG CCATTCTGTC
    ATACTTCACA GTTCCTCCTT GGGGAAGTAC ATACGGGGTC GGTAAGACAG 410        420        430        440        450
    CTTGGCTGCT CAGTACGACA AGGTCGTTCT GGCATGCTGC AAAGCTGACA
    GAACCGACGA GTCATGCTGT TCCAGCAAGA CCGTACGACG TTTCGACTGT 460        470        480        490        500
    ACAAGGAGGA GTGCTTCCAG ACAAAGAGAG CATCCATTGC AAAGGAATTA
    TGTTCCTCCT CACGAAGGTC TGTTTCTCTC GTAGGTAACG TTTCCTTAAT 510        520        530        540        550
    AGAGAAGGAA GCATGTTAAA TGAGCATGTA TGTTCAGTGA TAAGAAAATT
    TCTCTTCCTT CGTACAATTT ACTCGTACAT ACAAGTCACT ATTCTTTTAA 560        570        580        590        600
    TGGATCCCGA AACCTCCAGG CAACAACCAT TATTAAGCTA AGTCAAAAGT
    ACCTAGGGCT TTGGAGGTCC GTTGTTGGTA ATAATTCGAT TCAGTTTTCA 610        620        630        640        650
    TAACTGAAGC AAATTTTACT GAGATTCAGA AGCTGGCCCT GGATGTGGCT
    ATTGACTTCG TTTAAAATGA CTCTAAGTCT TCGACCGGGA CCTACACCGA 660        670        680        690        700
    CACATCCACG AGGAGTGTTG CCAAGGAAAC TCGCTGGAGT GTCTGCAGGA
    GTGTAGGTGC TCCTCACAAC GGTTCCTTTG AGCGACCTCA CAGACGTCCT 710        720        730        740        750
    TGGGGAAAAA GTCATGACAT ATATATGTTC TCAACAAAAT ATTCTGTCAA
    ACCCCTTTTT CAGTACTGTA TATATACAAG AGTTGTTTTA TAAGACAGTT 760        770        780        790        800
    GCAAAATAGC AGAGTGCTGC AAATTACCCA TGATCCAACT AGGCTTCTGC
    CGTTTTATCG TCTCACGACG TTTAATGGGT ACTAGGTTGA TCCGAAGACG 810        820        830        840        850
    ATAATTCACG CAGAGAATGG CGTCAAACCT GAAGGCTTAT CTCTAAATCC
    TATTAAGTGC GTCTCTTACC GCAGTTTGGA CTTCCGAATA GAGATTTAGG 860        870        880        890        900
    AAGCCAGTTT TTGGGAGACA GAAATTTTGC CCAATTTTCT TCAGAGGAAA
    TTCGGTCAAA AACCCTCTGT CTTTAAAACG GGTTAAAAGA AGTCTCCTTT 910        920        930        940        950
    AAATCATGTT CATGGCAAGC TTTCTTCATG AATACTCAAG AACTCACCCC
    TTTAGTACAA GTACCGTTCG AAAGAAGTAC TTATGAGTTC TTGAGTGGGG 960        970        980        990       1000
    AACCTTCCTG TCTCAGTCAT TCTAAGAATT GCTAAAACGT ACCAGGAAAT
    TTGGAAGGAC AGAGTCAGTA AGATTCTTAA CGATTTTGCA TGGTCCTTTA
```

-continued

```
         1010       1020       1030       1040       1050
    ATTGGAGAAG TGTTCCCAGT CTGGAAATCT ACCTGGATGT CAGGACAATC
    TAACCTCTTC ACAAGGGTCA GACCTTTAGA TGGACCTACA GTCCTGTTAG 1060       1070       1080       1090       1100
    TGGAAGAAGA ATTGCAGAAA CACATCGAGG AGAGCCAGGC ACTGTCCAAG
    ACCTTCTTCT TAACGTCTTT GTGTAGCTCC TCTCGGTCCG TGACAGGTTC 1110       1120       1130       1140       1150
    CAAAGCTGCG CTCTCTACCA GACCTTAGGA GACTACAAAT TACAAAATCT
    GTTTCGACGC GAGAGATGGT CTGGAATCCT CTGATGTTTA ATGTTTTAGA 1160       1170       1180       1190       1200
    GTTCCTTATT GGTTACACGA GGAAAGCCCC TCAGCTGACC TCAGCAGAGC
    CAAGGAATAA CCAATGTGCT CCTTTCGGGG AGTCGACTGG AGTCGTCTCG 1210       1220       1230       1240       1250
    TGATCGACCT CACCGGGAAG ATGGTGAGCA TTGCCTCCAC GTGCTGCCAG
    ACTAGCTGGA GTGGCCCTTC TACCACTCGT AACGGAGGTG CACGACGGTC 1260       1270       1280       1290       1300
    CTCAGCGAGG AGAAATGGTC CGGCTGTGGT GAGGGAATGG CCGACATTTT
    GAGTCGCTCC TCTTTACCAG GCCGACACCA CTCCCTTACC GGCTGTAAAA 1310       1320       1330       1340       1350
    CATTGGACAT TTGTGTATAA GGAATGAAGC AAGCCCTGTG AACTCTGGTA
    GTAACCTGTA AACACATATT CCTTACTTCG TTCGGGACAC TTGAGACCAT 1360       1370       1380       1390       1400
    TCAGCCACTG CTGCAACTCT TCGTATTCCA ACAGGAGGCT ATGCATCAAA
    AGTCGGTGAC GACGTTGAGA AGCATAAGGT TGTCCTCCGA TACGTAGTGG 1410       1420       1430       1440       1450
    AGTTTTCTGA GGGATGAAAC CTATGCCCCT CCCCCATTCT CTGAGGATAA
    TCAAAAGACT CCCTACTTTG GATACGGGGA GGGGGTAAGA GACTCCTATT 1460       1470       1480       1490       1500
    ATTCATCTTC CACAAGGATC GTGCCAAGCT CGGCAAAGCC CTACAGACCA
    TAAGTAGAAG GTGTTCCTAG CACGGTTCGA GCCGTTTCGG GATGTCTGGT 1510       1520       1530       1540       1550
    TGAAACAAGA GCTTCTCATT AACCTGGTGA AGCAAAAGCC TGAACTGACA
    ACTTTGTTCT CGAAGAGTAA TTGGACCACT TCGTTTTCGG ACTTGACTGT 1560       1570
    GAGGAGCAGC TGGCGGCTGT CACTGCAG
    CTCCTCGTCG ACCGCCGACA GTGACGTC
```

The rat α-fetoprotein 3' end cDNA is as follows (540 bp's):

```
         10         20         30         40         50
    GAGGGACTGG CCGACATTTA CATTGGACAC TTGTGTTTAA GACATGAGGC
    CTCCCTGACC GGCTGTAAAT GTAACCTGTG AACACAAATT CTGTACTCCG 60         70         80         90        100
    AAACCCTGTG AACTCCGGTA TCAACCACTG CTGCAGTTCC TCGTATTCCA
    TTTGGGACAC TTGAGGCCAT AGTTGGTGAC GACGTCAAGG AGCATAAGGT 110        120        130        140        150
    AGAGGAGGCT CTGCATCACC AGCTTTCTGA GGGACGAAAC CTACGTCCCT
    TGTCCTCCGA GACGTAGTGG TCGAAAGCAT CCCTGCTTTG GATGCAGGGA 160        170        180        190        200
    CTACCATTCT CTGCGACAAA TTCATCTTCC ACAAGGAATC TGTGCCAAGC
    GATGGTAAGA GACGCTGTTT AAGTAGAAGG TGTTCCTTAG ACACGGTTCG 210        220        230        240        250
    TCAGGGCCGA GCACCACAGA CCATGAAACA AGAGCTTCTC ATTAACCTAG
    AGTCCCGGCT CGTGGTGTCT GGTACTTTGT TCTCGAAGAG TAATTGGATC 260        270        280        290        300
    TGAAACAAAA GCCTGAAATG ACAGAGGAGC AGCACGCGGC TGTCACTGCT
    ACTTTGTTTT CGGACTTTAC TGTCTCCTCG TCGTGCGCCG ACAGTGACGA 310        320        330        340        350
    GATTTCTCTG GCCTCTTGGA GAAGTGCTGC AAAGACCAGG ATCAGGAAGC
    CTAAAGAGAC CGGAGAACCT CTTCACGACG TTTCTGGTCC TAGTCCTTCG
```

-continued

```
         360        370        380        390        400
    CTGTTTCGCA AAAGAGGTCC AAGTTGATTT CCAAACTCGT GAGGCTTTGG
    GACAAAGCGT TTTCTCCAGG TTCAACTAAA GGTTTGAGCA CTCCGAAACC 410        420        430        440        450
    GGGTTTAAAC ATCTCCAAGA GGAAGAAAGG ACAAAAAAAT GTGTCGACGC
    CCCAAATTTG TAGAGGTTCT CCTTCTTTCC TGTTTTTTTA CACAGCTGCG 460        470        480        490        500
    TTTGGTGTGA GCTTTTCGGT TTGATGGTAA CTGGTGGAGA CTTCCATGTG
    AAACCACACT CGAAAAGCCA AACTACCATT GACCACCTCT GAAGGTACAC 510        520        530        540
    GGATTTCTAT GCCTAAGGAA TAAAGACTTT TCAACTGTTA
    CCTAAAGATA CGGATTCCTT ATTTCTGAAA AGTTGACAAT
```

The homologous region between both is as follows, (human: upper; rat: lower):

```
          ***              *       *   *    *       *
1367  CTCTTCGTATTCCAACAGGAGGCTATGCATCACCAG-TTTTCTGAGGGATGAAACCTATG
  90  CTC---GTATTCCAACAGGAGGCTCTGCATCACCAGCTTT-CTGAGGGACGAAACCTACG

*    **  *          **   **   *                      *   *
      CCCCTC-CCCCATTCTCTGAGGA-TAAATTCATCTTCCACAAGGA-TC-GTGCCAAGCTC
      TCCCTCTACC-ATTCTCTG-CGACAAA-TTCATCTTCCACAAGGAATCTGTGCCAAGCTC

*  ** * *    *  *                                   *    *
      -GG--CAAAGC-CCTACAGACCATGAAACAAGAGCTTCTCATTAACCTGGTGAAGCAAAA
      AGGGCCGA-GCACC-ACAGACCATGAAACAAGAGCTTCTCATTAACCTAGTGAAACAAAA

*            **
      GCCTGAACTGACAGAGGAGCAGCTGGCGGCTGTCACTGC    1576
      GCCTGAAATGACAGAGGAGCAGCACGCGGCTGTCACTGC     299
```

% = 85.845
P(219, 188) = .000E+00  E = .000

Restriction sites for both human and rat are as follows:

| | HUMAN | | | | | | |
|---|---|---|---|---|---|---|---|
| MboII (GAAGA) | 108 | 261 | 328 | 1066 | 1069 | 1230 | |
| MboII (TCTTC) | 881 | 916 | 1361 | 1449 | | | |
| MnlI (CCTC) | 273 | 574 | 1190 | 1200 | 1219 | 1245 | 1439 |
| MnlI (GAGG) | 44 | 47 | 358 | 449 | 653 | 887 | 1070 | 1162 |
| | 1250 | 1274 | 1378 | 1402 | 1436 | 1544 | |
| | RAT | | | | | | |
| MboII (GAAGA) | 435 | | | | | | |
| MboII (TCTTC) | 168 | | | | | | |
| MnlI (CCTC) | 100 | 159 | 323 | | | | |
| MnlI (GAGG) | 39 | 98 | 122 | 267 | 357 | 384 | 412 |

It can be calculated that fragments containing a portion of the conserved sequence, 24, 34, 104 and 108 bp describe the human DNA. Fragments of 24, 59, 90 and 145 describe the rat DNA. While both sequences contain the 24 bp fragment, it is the set of fragments (taxonomic characters) that is of significance.

Having now fully described this invention, it will be apparent to one of ordinary skill in the art that many variations and permutations can be carried within a wide range of equivalents without effecting the spirit or scope of the invention, or of any embodiments thereof.

What is claimed as new and desired to be secured by Letters Patent of the United States is:

1. A kit for establishing the species of an unknown organism, said kit comprising a carrier being compartmentalized to receive in close confinement therein:

a. at least one container containing an isolated, detectably labeled nucleic acid selected from the group consisting of ribosomal RNA (rRNA), DNA, and cDNA derived from said rRNA, wherein said nucleic acid:

(1) is selected from the group consisting of prokaryotic ribosomal nucleic acid, eukaryotic mitochondrial ribosomal nucleic acid, eukaryotic chromosomal ribosomal nucleic acid, and eukaryotic non-organelle ribosomal nucleic acid, and (2) is capable of hybridizing to restriction endonuclease digested DNA from said unknown organism, whereby a chromatographic band pattern is produced; and b. information storage means selected from the group consisting of a catalog, a computer tape, a computer disk, a computer memory, and a computer access number, wherein are stored at least fifty chromatographic band patterns representing the hybridization of said isolated, detectably labeled nucleic acid to restriction endonuclease digested DNA from more than one representative strain of at least two known different organism species, each pattern in the information storage means being conserved among different strains of a specific organism species, but not conserved among different organism species, whereby the band pattern of said unknown organism can be compared with the stored band patterns, thereby enabling the species of the unknown organism to be established.

2. The kit of claim 1 further comprising a container containing one or more restriction endonuclease enzymes.

3. The kit of claim 1 further comprising a container containing one or more detectably labeled deoxynucleoside triphosphates.

4. The kit of claim 1 or 2 wherein said nucleic acid is of a prokaryotic origin.

5. The kit of claim 1 or 2 wherein said nucleic acid is selected from the group consisting of eukaryotic mitochondrial ribosomal nucleic acid, eukaryotic chromosomal ribosomal nucleic acid, and eukaryotic non-organelle ribosomal nucleic acid.

6. The kit of claim 4 wherein said prokaryote is a bacterium.

7. The kit of claim 5 wherein said nucleic acid is eukaryotic mitochondrial ribosomal nucleic acid.

8. The kit of claim 1 or 2 wherein said nucleic acid is labeled with $^{32}P$, $^{14}C$, or $^{3}H$.

9. The kit of claim 1 or 2 further comprising one or more containers containing viral nucleic acid probes.

10. The kit of claim 1 or 2 wherein said information storage means also include viral chromatographic patterns.

11. The kit of claim 1 or 2 wherein said information storage means contains between 50 and 150 chromatographic band patterns.

* * * * *

UNITED STATES PATENT AND TRADEMARK OFFICE
CERTIFICATE OF CORRECTION

PATENT NO. : 5,614,361
DATED : March 25, 1997
INVENTOR(S) : John A. Webster, Jr.

It is certified that error appears in the above-identified patent and that said Letters Patent is hereby corrected as shown below:

On the title page:

column 1, at item [75] ("Inventors"), delete "8343 Carrleigh Parkway, Springfield, Va. 22152" and insert therefor --1013 Dunvegan Road, West Chester, PA 19382--.

column 2, at lines 36-37, delete "ribounucleic" and insert therefor --ribonucleic--.

column 2, at line 7, delete "370" and insert therefor --270--.

column 2, at line 35, delete "Col." and insert therefor --Co.--.

column 2, at line 56, italicize the two words "Chromobacterium" and "Janthinobacterium".

column 2, at line 3, delete "(19833)" and insert therefor --(1983)--.

column 2, at line 58, delete "65" and insert therefor --64--.

column 1, at line 8, delete "Nuber" and insert therefor --Number--.

column 2, at line 3, delete "626" and insert therefor --625--.

Figures 11A, 11B:
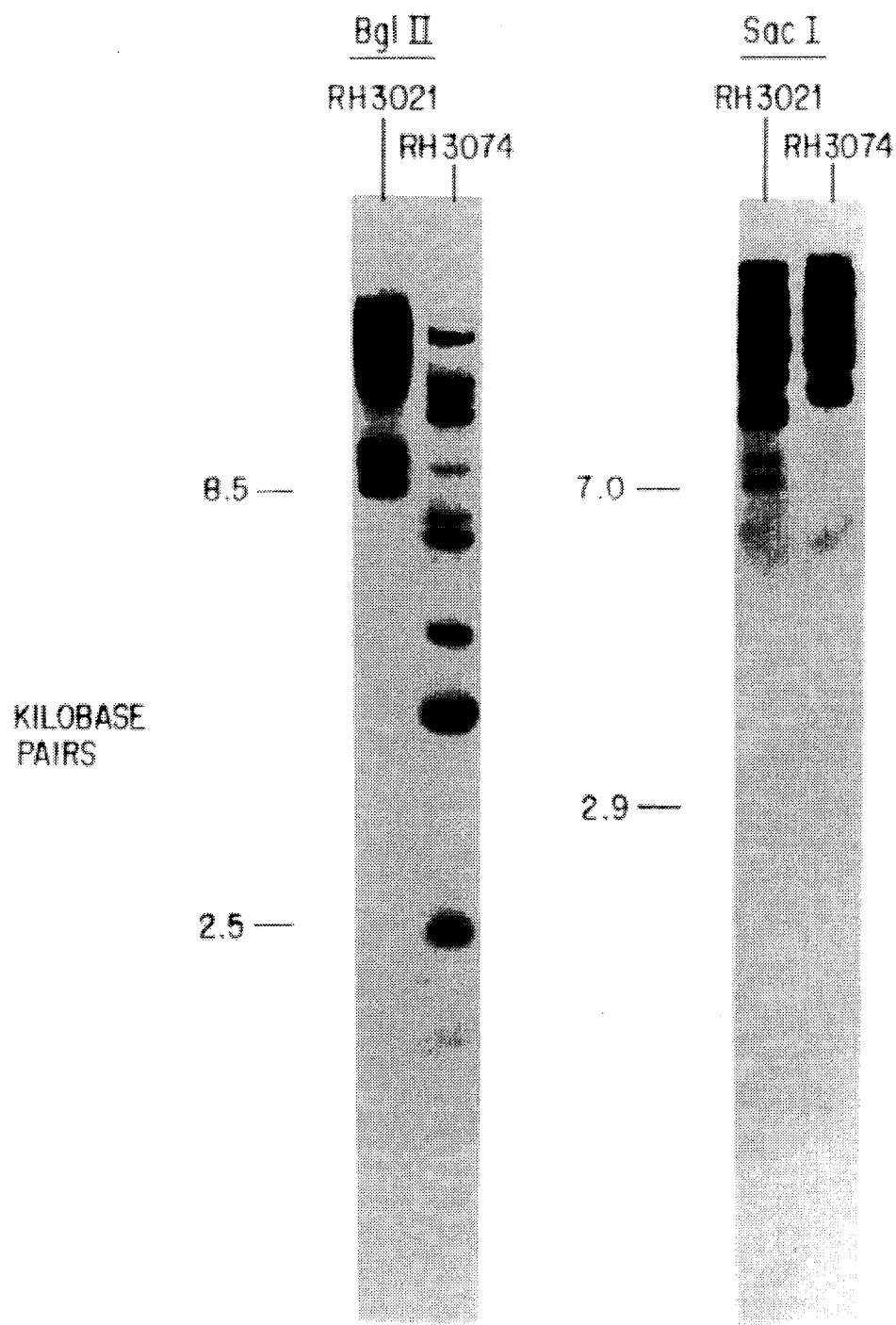
FIG. 11 shows the Bgl II and Sac I data for the same strains as in FIGS. 9 and 10, with the same probe.

In Column 5, at line 23, delete "FIG. 11 shows" and insert therefor --FIGS. 11A and 11B show--.

UNITED STATES PATENT AND TRADEMARK OFFICE
CERTIFICATE OF CORRECTION

PATENT NO. : 5,614,361
DATED : March 25, 1997
INVENTOR(S) : John A. Webster, et al It is certified that error appears in the above-identified patent and that said Letters Patent is hereby corrected as shown below:

In Column 5, at line 25, delete "FIG. 12 shows" and insert therefor --FIGS. 12A, 12B, 12C, and 12D show--.

In Column 23, at lines 30-31, make "Synthesis of $^{32}$P ribosomal RNA Complementary DNA ($^{32}$P rRNA cDNA)." a new paragraph.

In Column 27, at line 38, delete "R.E" and insert therefor --R.E.--.

In Column 27, at line 45, delete "ever,".

Signed and Sealed this

Twenty-eighth Day of April, 1998

*Attest:*

BRUCE LEHMAN

*Attesting Officer*  Commissioner of Patents and Trademarks